United States Patent
Bakare et al.

(10) Patent No.: US 9,422,231 B2
(45) Date of Patent: Aug. 23, 2016

(54) **METHOD FOR INHIBITING *TRYPANOSOMA CRUZI***

(75) Inventors: Oladapo Bakare, Beltsville, MD (US); Clarence M. Lee, Mitchellville, MD (US); Yakini Brandy, Hyattsville, MD (US); Mozna Husein Khraiwesh, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 14/235,273

(22) PCT Filed: Jul. 27, 2012

(86) PCT No.: PCT/US2012/048616
§ 371 (c)(1),
(2), (4) Date: Apr. 10, 2014

(87) PCT Pub. No.: WO2013/016661
PCT Pub. Date: Jan. 31, 2013

(65) Prior Publication Data
US 2015/0073177 A1    Mar. 12, 2015

Related U.S. Application Data

(60) Provisional application No. 61/512,232, filed on Jul. 27, 2011.

(51) Int. Cl.
| | | |
|---|---|---|
| *C07C 235/88* | (2006.01) | |
| *A61K 31/122* | (2006.01) | |
| *C07C 50/32* | (2006.01) | |
| *C07C 217/94* | (2006.01) | |
| *C07C 225/30* | (2006.01) | |

(52) U.S. Cl.
CPC .............. *C07C 235/88* (2013.01); *A61K 31/122* (2013.01); *C07C 50/32* (2013.01); *C07C 217/94* (2013.01); *C07C 225/30* (2013.01)

(58) Field of Classification Search
CPC ...................................................... C07C 235/88
See application file for complete search history.

(56) References Cited

U.S. PATENT DOCUMENTS

| 4,829,089 A | 5/1989 | Medwid et al. |
| 4,942,170 A | 7/1990 | Henderson et al. |
| 2011/0110891 A1 | 5/2011 | Ott et al. |

FOREIGN PATENT DOCUMENTS

WO    0008495 A2    2/2000

OTHER PUBLICATIONS

Akinboye et al, Acta Crystallographia Section E, E65, o77 including supplementary materials (2009).
Mozna H. Khraiwesh et al., "Antitrypanosomal Activities and Cytotoxicity of Some Novel Imidosubstituted 1,4-Naphthoquinone Derivatives", Arch Pharm Res, vol. 35, No. 1, pp. 27-33, 2012.
International Search Report, dated Oct. 1, 2012, issued against International Application PCT/US2012/048616.

(Continued)

*Primary Examiner* — Clinton Brooks
(74) *Attorney, Agent, or Firm* — Fitch, Even, Tabin & Flannery LLP

(57) ABSTRACT

Methods are provided to inhibit proliferation of *Trypanosoma cruzi* with imido-substituted 1,4-naphthoquinones, including novel compounds. Administering an imido-substituted 1,4-naphthoquinone can be used to provide prophylaxis or treatment to a patient in need of treatment against Chagas disease.

26 Claims, 29 Drawing Sheets

(56) References Cited

OTHER PUBLICATIONS

PCT—Written Opinion of the International Search Authority issued in International Application PCT/US2012/048616.

Y. Brandy, et al., "Design & Synthesis of Non-Cyclic Imido-Substituted 2-Chloro 1,4-Naphthoquinone Derivatives as Mek1 Inhibitors and Potential Anticancer Agents," The 35th Annual Conference of the National Organization for the Professional Advancement of Black Chemists and Chemical Engineers, Abstract, No. 67, Mar. 16-21, 2008.

E. Ramos, et al., 2, 3-Dlphenyl-1,4-Naphthoquinone: A Potentional Chemotherapeutic Agent Against Trypanosoma Cruzi, J Parasitol. Apr. 2009; 95(2): 461-466. doi: 10.1645/GE-1686.1.

A. Pinto, et al., The Trypanocidal Activity of Naphthoquinones: A Review, Molecules 2009, 14, 4570-4590; doi; 10.3390/molecules14114570.

FIG. 6A

| 3,5-Bis (trifluoromethyl) benzoyl chloride | benzoyl chloride | 2-bromobenzoyl chloride | 2-fluorobenzoyl chloride |
|---|---|---|---|

| 2,4-difluorobenzoyl chloride | 2,6 difluorobenzoyl chloride | 2-chlorobenzoyl chloride | 2,4-dichlorobenzoyl chloride |
|---|---|---|---|

| 2,6-dichlorobenzoyl chloride | O-Acetylsalicyloyl chloride | 2-methoxybenzoyl chloride | 2,6-dimethoxybenzoyl chloride |
|---|---|---|---|

| 2-(trifluoromethyl)benzoyl chloride | o-toluoyl chloride | 3-bromobenzoyl chloride | 3-fluorobenzoyl chloride, 95% |
|---|---|---|---|

| 3-chlorobenzoyl chloride | 3,4-dichlorobenzoyl chloride | 3-methoxybenzoyl chloride, 99% | 3,4-dimethoxybenzoyl chloride |
|---|---|---|---|

FIG. 6B 3,4,5-trimethoxybenzoyl chloride  3-ethoxybenzoyl chloride
3,5-dimethoxylbenzoyl chloride  3-(trifluomethyl)benzoyl chloride

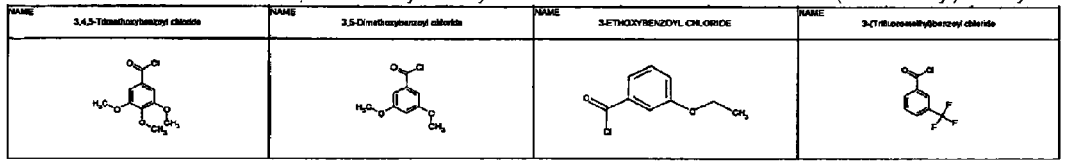

3-(chloromethyl)benzoyl chloride
m-toluoyl chloride  4-bromobenzoyl chloride  4-fluorobenzoyl chloride

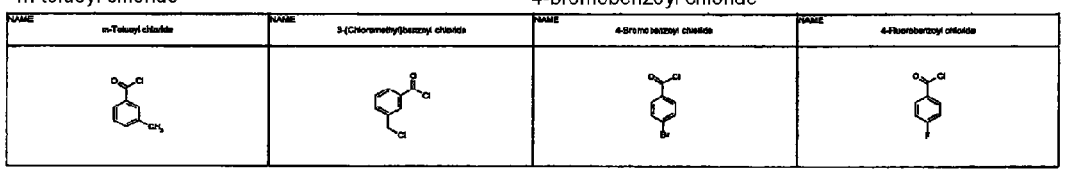

4-chlorobenzoyl chloride  4-ethoxybenzoyl chloride, 98%
4-methoxybenzoyl chloride  4-butoxybenzoyl chloride

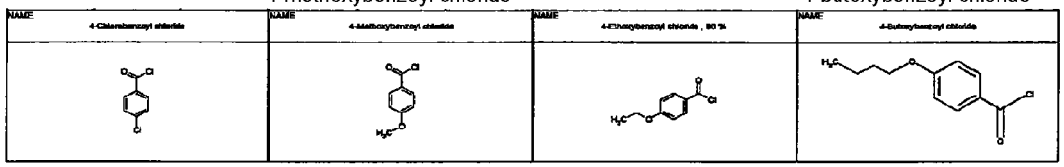

4-(heptyloxy)benzoyl chloride  4-(trifluoromethyl)benzoyl chloride
4-hexyloxy)benzoyl chloride  bi-phenyl-4carboxyl chloride

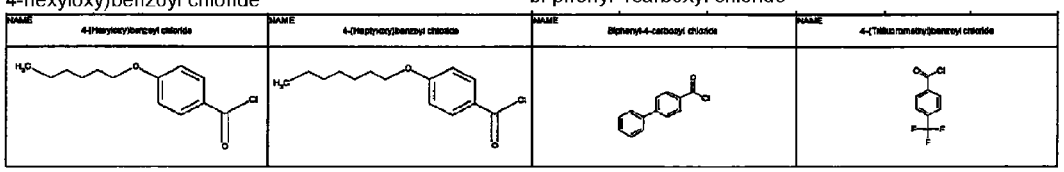

p-toluoyl chloride  4-propylbenzoyl chloride
4-tert-butylbenzoyl chloride  4-ethylbenzoyl chloride

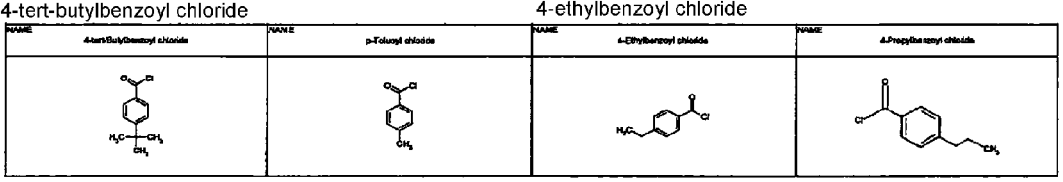

FIG. 6F

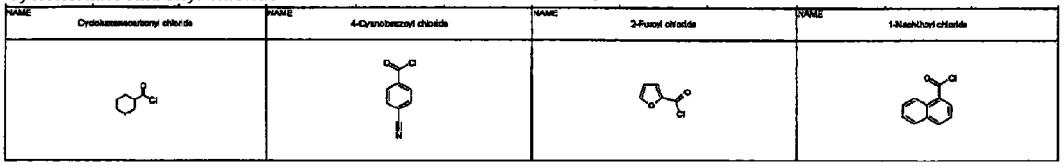
cyclohexanecarbonyl chloride | 4-cyanobenzoyl chloride | 2-furoyl chloride | 1-naphthoyl chloride

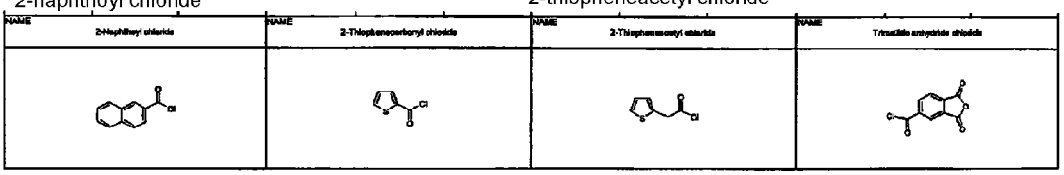
2-naphthoyl chloride | 2-thiophenecarbonyl chloride | 2-thiopheneacetyl chloride | trimallitio anhydride chloride

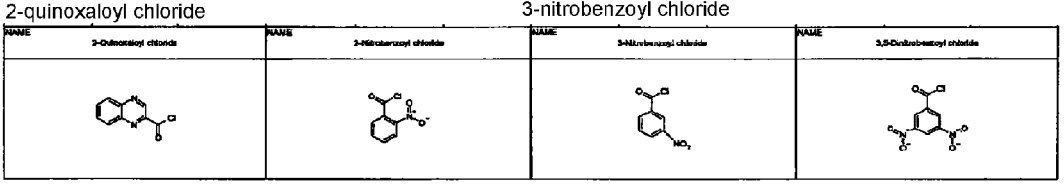
2-quinoxaloyl chloride | 2-nitrobenzoyl chloride | 3-nitrobenzoyl chloride | 3,5-dimitrobenzoyl chloride

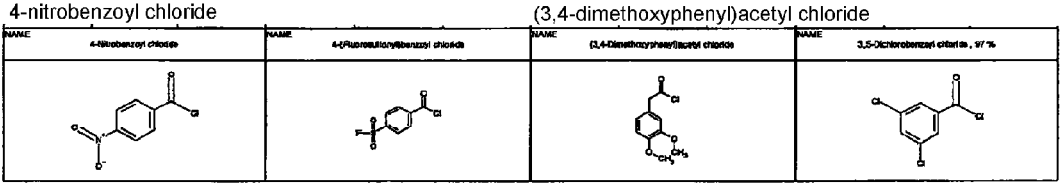
4-nitrobenzoyl chloride | 4-(fluorosulfonyl)benzoyl chloride | (3,4-dimethoxyphenyl)acetyl chloride | 3,5-dichlorobenzoyl chloride, 97%

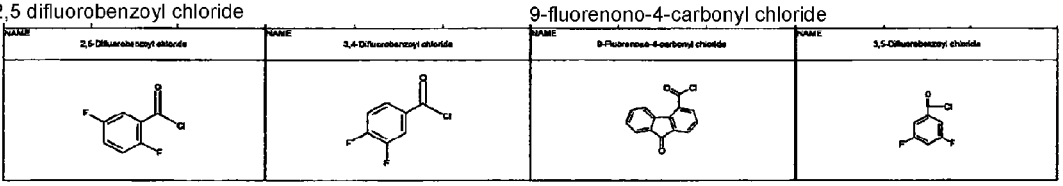
2,5 difluorobenzoyl chloride | 3,4-difluorobenzoyl chloride | 9-fluorenono-4-carbonyl chloride | 3,5-difluorobenzoyl chloride

FIG. 6H

| 2-phenylbutyryl chloride, 96% | 2-ethylbutyryl chloride | p-toly-acetyl chloride | 4-chloro-3-nitrobenzoyl chloride |
|---|---|---|---|
|  |  |  |  |

| 4-methyl-3-nitrobenzoyl chloride | 2,5-dichlorobenzoyl chloride | 2,3-dichlorobenzoyl chloride | 4-chlorophenylacetyl chloride |
|---|---|---|---|
|  |  |  |  |

| (R)-(-)-2-phenylglycine chloride hydrochloride | 2-chlorocinnamoyl chloride | 5-nitro-2-furoyl chloride | 6-chlorohexanoyl chloride |
|---|---|---|---|
|  | 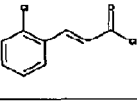 |  |  |

| 2,5-dichlorothiophene-3-carbonyl chloride | 4-(phenylazo)benzoyl chloride | 4-n-pentyloxybenzoyl chloride, 97% | p-decylbenzoyl chloride |
|---|---|---|---|
| 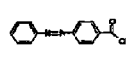 |  | 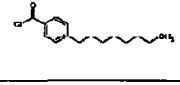 |  |

| 4-octylbenzoyl chloride, 99% | 2,3-difluorobenzoyl chloride | 2-(benzoyloxymethyl)benzoyl chloride | (R)-(-)-alpha-methoxy-alpha-(trifluoromethyl)phenylacetyl chloride |
|---|---|---|---|
|  | | | |

FIG. 6J

| 3-(2,6-dichlorophenyl)-5-methylisoxazole-4-carbonyl chloride | 2,6-dichloropyridine-4-carbonyl chloride | 2-phenoxypyridine-3-carbonyl chloride | 2-(propylthio)pyridine-3-carbonyl chloride, 97% |
|---|---|---|---|
| 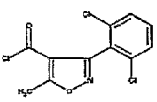 |  | 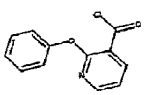 |  |

| 2-chloro-6-methylpyridine-4-carbonyl chloride | 3-chlorobenzo(b)thiophene-2-carboryl chloride | 4-(chloromethyl)benzoyl chloride | (phanylthio)acetyl chloride |
|---|---|---|---|
|  |  | 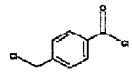 |  |

| ethyl hexafluoroglutaryl chloride, 97% | 3-(2-chloro-6-fluorophenyl)-5methylisoxazole-4-carbonyl chloride | behenoyl chloride | tridacanoyl chloride |
|---|---|---|---|
| 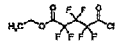 |  | 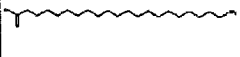 |  |

| 2-chloro-5-nitrobenzoyl chloride | 3-methylthiopropionyl chloride, >98.0% | terephthalic acid monomethyl ester chloride | anthraquinone-2-carbonyl chloride, >98 |
|---|---|---|---|
|  |  |  |  |

| 2-nitrophenoxyacetyl chloride | picolinoyl chloride hydrochloride | 2-fluoro-3-(trifluoromethyl)benzoyl chloride | 2-fluoro-4-(trifluoromethyl)benzoyl chloride |
|---|---|---|---|
|  |  |  |  |

FIG. 6M

| 1-benzyl-3-(tert-butyl)-1h-pyrazole-5-carbonyl chloride, 95% | 1-(tert-butyl)-3-methyl-1h-pyrazole-5-carbonyl chloride | 3-(tert-butyl)-1-methyl-1h-pyrazole-5-carbonyl chloride | 2-chloro-4-fluorobenzoyl chloride |
|---|---|---|---|

| 3-chloro-4-(isopropylsulfonyl)thiophene-2-carbonyl chloride | 5-methylisoxazole-3-carbonyl chloride | (E)-2-methyl-3-phenyl-acryloyl chloride | [(dipropylamino)sulfonyl]benzene-1-carbonyl chloride |
|---|---|---|---|

| 6-bromo-2-chlroquinoline-4-carbonyl chloride | 2-chloro-6-methoxypyridine-4-carbonyl chloride | (4-bromo-phenyl)-acetyl chloride | 2-(4-chlorophenoxy)-2-methylpropanoyl chloride |
|---|---|---|---|

| 3-thiophenecarbonyl chloride | 3-methylthiophene-2-carbonyl chloride | 5-methyl-thiophene-2-carbonyl chloride | oleoyl chloride |
|---|---|---|---|

| methyl-6-chloro-6-oxaoctanoate | (1S)-(-)camphanic chloride | (1R)-(+)-camphanic chloride | 7-[(chlorocarbonyl)methoxy]-4-methylcoumarin |
|---|---|---|---|

FIG. 6N

| (s)-(-)-2-acetoxyproplonyl chloride | linoleoyl chloride | 7h-dodecafluoroheptanoyl chloride | 5h-octafluoropentanoyl chloride |
|---|---|---|---|

| 2,2,3,3-tetrafluoropropionyl chloride | arachidonoyl chloride | nonafluoropentanoyl chloride | tridecafluoroheptanoyl chloride |
|---|---|---|---|

| 4-bromo-1-ethyl-3-methyl-1h-pyrazole-5-carbonyl chloride | 2-chloro-4-(trifluoromethyl)pyrimidine 5-carbonyl chloride, 97% | 4-methyl-1,2,3-thiadiazole-5-carbonyl chloride | 5-bromonicotinoyl chloride |
|---|---|---|---|

| 1-phenyl-5-propyl-1h-pyrazole-4-carbonyl chloride, 97% | 1-(4-nitrophenyl)-5-(trifluoromethyl) pyrazole-4-carbonyl chloride, 85+% | 3-chloro-4-(methylsulfonyl) thiophene-2-carbonyl chloride | 2-(1-naphthyl)ethanoyl chloride |
|---|---|---|---|

| 2-chloro-6-fluorobenzoyl chloride | n-[7-(n,n-dimethylsulfamoyl)-4-benzofurazanyl]methylamino-acetyl chloride | n-(1-naphthalenesulfonyl)-l-phenylalanyl chloride | n-(4-nitrophenylsulfonyl)-l-phenylalanyl chloride |
|---|---|---|---|

FIG. 6P

| 4-fluorophenylacetyl chloride | 4-benzyloxyphenylacetyl chloride | 2-pyrazinecarbonyl chloride | 2,4-dimethylbenzoyl chloride |
|---|---|---|---|

| (R)-(-)-o- formylmandeloyl chloride | 4-pentenoyl chloride | tigloyl chloride | 3,3,3-trifluoropropionyl chloride |
|---|---|---|---|

| 1,3-dimethylpyrazole-5-carbonyl chloride | 4-(difluoromethoxy)benzoyl chloride | 4-bromo-3-methylbenzoyl chloride, 99% | 2-(2,3-dihydro-1-benzofuran-5-yl)-4-methyl-1,3-thiazole-5-carbonyl chloride |
|---|---|---|---|

| 2-methylhexanoyl chloride | 2,3,4,5,6-pentafluorophenoxyacetyl chloride | 2-(2,3-dihydro-1-benzofuran-5-yl) thiazole-4-carbonyl chloride | 3-chloro-2,6-difluoro benzoyl chloride, 97% |
|---|---|---|---|

| 2,6-difluoro-3-methylbenzoyl chloride | 3-chloro-2-fluoro-6-(trifluoromethyl) benzoyl chloride | 5-chloro-2-(trifluoromethyl) benzoyl chloride | 2-chloro-6-fluoro-3-methylbenzoyl chloride |
|---|---|---|---|

FIG. 6Q

| 6-chloro-2-fluoro-3-methylbenzoyl chloride | 2-chloro-5-fluorobenzoyl chloride | 4-fluoro-3-methylbenzoyl chloride | 5-chloro-2-fluorobenzoyl chloride |
|---|---|---|---|

| 2-chloro-3,6-difluorobenzoyl chloride | 3-chloro-2,4-difluorobenzoyl chloride | 2,2-difluoro-1,3-benzodioxole-4-carbonyl chloride | 2,2-difluoro-1,3-benzodioxole-5-carbonyl chloride |
|---|---|---|---|

| 3-chloro-2-fluoro-5-(trifluoromethyl)benzoyl chloride | 2-(difluoromethylthio)benzoyl chloride | 3-(difluoromethylthio)benzoyl chloride | 4-methoxy-3-(trifluoromethyl)benzoyl chloride |
|---|---|---|---|

| 4-methyl-3-(trifluoromethyl)benzoyl chloride | 4-(trifluoromethylthio)benzoyl chloride | 2-chloro-5-(trifluoromethyl)benzoyl chloride | 2,3-difluoro-4-methylbenzoyl chloride |
|---|---|---|---|

| benzofuran-2-carbonyl chloride | 1,2,3-benzothiadiazole-5-carbonyl chloride | 5-(trifluoromethyl)nicotinoyl chloride | 2,4-dibromobutyryl chloride |
|---|---|---|---|

FIG. 6R

| 2,6-dichloro-5-fluoro-3-pyridine-carbonyl chloride | 2-bromophenylacetyl chloride | isonicotinoyl chloride | 2-(2,6-dichlorobenzyl)-1,3-thiazole-4-carbonyl chloride, 97% |
|---|---|---|---|

| 3-methylbenzofuran-2-carbonyl chloride | 3,5-dichloro-4-methoxy-benzoyl chloride | 3-chloro-6-fluorobenzo[b]thiophane-2-carbonyl chloride | 2-methyl-6-(trifluoromethyl)pyridine-3-carbonyl chloride |
|---|---|---|---|

| 6-chloro-2h-1-benzopyran-3-carbonyl chloride | 1-[4-(trifluoromethyl)pyrimidine-2yl]piperdine-4-carbonyl chloride | 1-methyl-1h-indazole-3-carbonyl chloride | 2,3,5,6-tetrafluorobenzoyl chloride |
|---|---|---|---|

| 3-iodobenzoyl chloride | 3,4,5-trichlorothiophene-2-carbonyl chloride, 97% | 2-(2-methoxyethoxy)acetyl chloride | 1-acetylpiperidine-4-carbonyl chloride |
|---|---|---|---|

| 3-chlorophenoxyacetyl chloride | 4-sulfamidobenzoyl chloride DMF complex | 1-methylpyrrole-2-carbonyl chloride | 4-acetamidobenzoyl chloride |
|---|---|---|---|

FIG. 6T

| 6-phenoxynicotinoyl chloride | 4-methyl-2-(2-pyrazinyl)-1,3-thiazole-5-carbonyl chloride | benzyl 2-(chlorocarbonyl)-1-indolinecarboxylate | 6-morpholinonicotinoyl chloride |
|---|---|---|---|

| 2-phenyl-1,3-thiazole-4-carbonyl chloride | 3-furoyl chloride | 5-phenyl-1,3-oxazole-4-carbonyl chloride | 2-(2-thienyl)-1,3-thiazole-4-carbonyl chloride |
|---|---|---|---|

| 6-quinoxalinecarbonyl chloride | 1-benzothiophene-3-carbonyl chloride | 2,4,5-trifluoro-3-methoxybenzoyl chloride | quinaldyl chloride |
|---|---|---|---|

| 9h-fluorene-9-carbonyl chloride | 2,3,4,5-tetrafluorobenzoyl chloride | 1-(phenylsulfonyl)-1h-indole 3-carbonyl chloride | 1-(phenylsulfonyl)-1h-indole-2-carbonyl chloride 97% |
|---|---|---|---|

| 4-methyl-3,4-dihydro-2h-1,4-benzoxazine-7-carbonyl chloride | 5-(2-methyl-1,3-thiazole-4-yl)-3-isoxazolecarbonyl chloride | 3-methyl-5-phenyl-4-isoxazolecarbonyl chloride | 1,3-dimethyl-1h-thieno[2,3-c] carbonyl chloride, 97% |
|---|---|---|---|

FIG. 6U

| 1-methyl-1h-1,2,3-benzotriazole-5-carbonyl chloride | 2,3-dihydro-1-benzofuran-2-carbonyl chloride | 2h-chromene-3-carbonyl chloride | 1-phenyl-1h-pyrazole-5-carbonyl chloride, 87% |
|---|---|---|---|
| 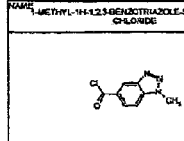 | 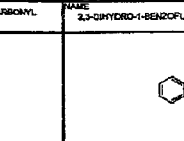 | 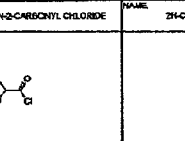 | 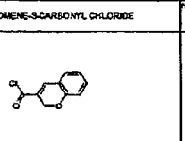 |

| 6-phenyl-1,3,4-oxadiazole-2-carbonyl chloride | 5-bromo-2,3,4-trimethyl-benzoyl chloride | 2,2-dimethylbutyryl chloride, 98% | 2-(4-chlorophenyl)-3-methylbutyryl chloride |
|---|---|---|---|
| 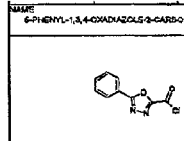 | 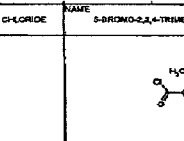 | 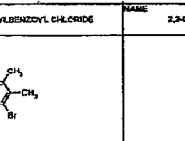 | 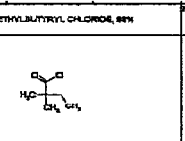 |

| 4-bromo-2,6-difluorobenzoyl chloride | 2-fluoro-5-iodobenzoyl chloride | 2-fluoro-6-iodobenzoyl chloride | 4-bromo-3-methyl-2-thiophene-carbonyl chloride |
|---|---|---|---|
| 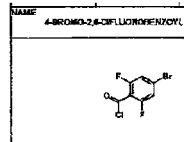 | 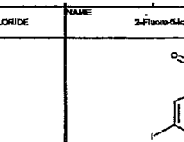 | 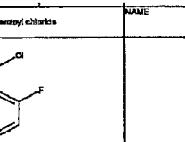 | 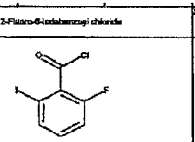 |

| 1-benzyloxycarbonylpiperidine-3-carbonyl chloride | 4-benzyl-2-morpholinecarbonyl chloride hydrochloride | 1-(4-chlorophenyl)-5-methyl-1h-pyrazole-4-carbonyl chloride | 3-methyl-5-(4-methyl-1,2,3-thiazol-5-yl)-4-isoxazole carbonyl chloride, 87% |
|---|---|---|---|
| 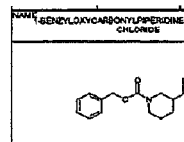 | 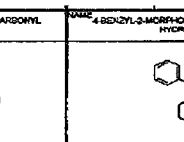 | 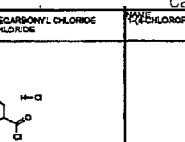 | 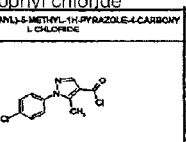 |

| 5-methyl-1(2-methylphenyl)-1h-pyrazole-4-carbonyl chloride, 97% | 3-(4-fluorophenyl)-5-methyl-4-isoxazolecarbonyl chloride | 3-(4-methoxyphenyl)-5-methyl-4-isoxazolecarbonyl chloride | 1,5-dimethyl-1h-pyrazole-3-varbonyl chloride |
|---|---|---|---|
| 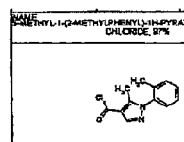 | 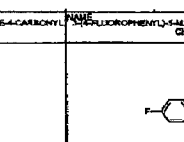 | 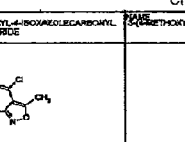 | 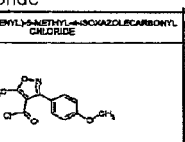 |

FIG. 6V

| 4-bromo-2-fluorobenzoyl chloride | 5-methyl-4-isoxazole-carbonyl chloride | 2,2,3,3-tetrafluoro-1-(methyl)cyclobutanecarbonyl chloride | 1-methyl-1h-pyrazole-5-carbonyl chloride |
|---|---|---|---|
| 5-methylfuran-2-carbonyl chloride | 2-methylfuran-3-carbonyl chloride | (5-methyl-3-trifluoromethyl-pyrazol-1-yl)-acetyl chloride | 3-maleimidobenzoic acid chloride |
| (4-chloro-3-methyl-pyrazol-1-yl)-acetyl chloride | 3-methoxy-propionyl chloride | cyclohexylacetyl chloride | 4-isopropyl-benzoyl chloride |
| 2,3-dimethoxy-benzoyl chloride | o-tolyl-acetyl chloride | (2,6-difluoro-phenyl)-acetyl chloride | (2,5-difluoro-phenyl)-acetyl chloride |
| 9h-xanthene-9-carbonyl chloride | benzo(1,3)dioxol-5-yl-acetyl chloride | 1-P-tolyl-cyclopentane-carbonyl chloride | 1-(4-methoxyphenyl)cyclopentane-carbonyl chloride |

FIG. 6W

| thiophen-3-yl-acetyl chloride | 3-phenyl-butyryl chloride | 3-(2-methoxy-phenyl)-propionyl chloride | 4-fluorocinnamoyl chloride |
|---|---|---|---|

| 5-bromo-furan-2-carbonyl chloride | 3-fluoro-4-methoxybenzoyl chloride | 1,3-benzothiazole-2-carbonyl chloride | 1-benzofuran-5-carbonyl chloride |
|---|---|---|---|

| 1-methyl-1h-imidazole-5-carbonyl chloride hydrochloride | 5-(4-methoxyphenyl)-1,3-oxazole-4-carbonyl chloride | 3,5-bis(trifluoromethyl)phenyl-acetyl chloride | 2-fluoro-6-methoxybenzoyl chloride |
|---|---|---|---|

| biphenyl-3-carbonyl chloride | 2-bromo-6-chlorobenzoyl chloride | 3,4-dihydro-2h-1,5-benzo-dioxepine-6-carbonyl chloride | 2,2-dimethyl-2,3-dihydro-1-benzo-furan-7-carbonyl chloride |
|---|---|---|---|

| 4-bromo-2-thiophenecarbonyl chloride | 5-chloro-1-methyl-3-(trifluoromethyl)-1h-pyrazole-4-carbonyl chloride | 5-nitro-1-benzothio-phene-2-carbonyl chloride 97% | 3-methyl-2-furoyl chloride |
|---|---|---|---|

FIG. 6X

| 2,3-dihydro-1,4-benzodioxine-5-carbonyl chloride | 1-benzothiophene-5-carbonyl chloride | 2,5-dimethyl-1,3-oxazole-4-carbonyl chloride | 5-tert-butyl-thiophene-2-carbonyl chloride |

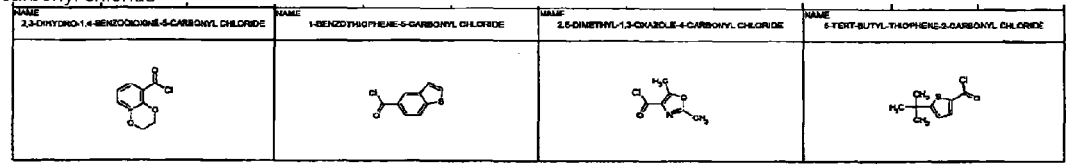

| 2,1,3-benzothiadiazole-4-carbonyl chloride | 5-bromo-2,3-dihydrobenzo[B]furan-7-carbonyl chloride | 2,5-diethoxybenzoyl chloride | pyrazolo[1,5-A]pyridine-3-carbonyl chloride |

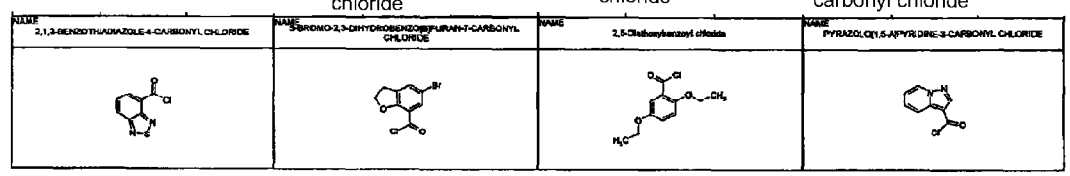

| tetrahydro-2h-pyran-4-carbonyl chloride | 1,3-thiazole-2-carbonyl chloride | 8-methyl-6-nonenoyl chloride | 4-(dichromethyl)benzoyl chloride |

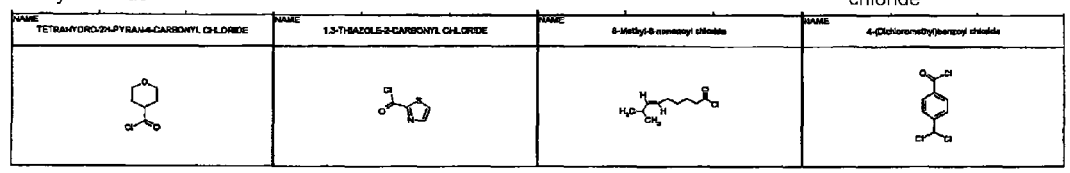

| 5-bromobenzo[B]thiophene-3-carbonylchloride | 4h-thieno[3,2-B]pyrrole-5-carbonyl chloride | 4-(methylthiol)benzoyl chloride | 4-(trifluoromethyl)phenylacetyl chloride |

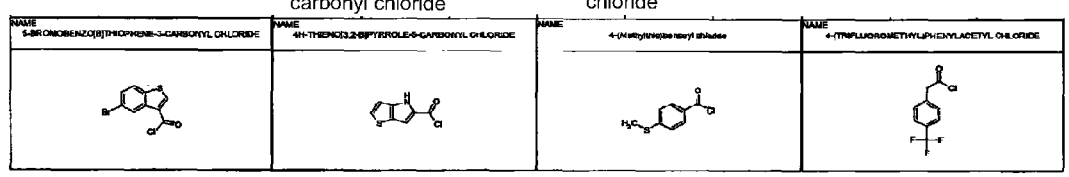

| 3-(trifluoromethyl)phenylacetyl chloride | 3,4-difluorophenylacetyl chloride | 2,4-difluorophenylacetyl chloride | 2-(trifluoromethyl)-2'-methoxy-phenylacetyl chloride |

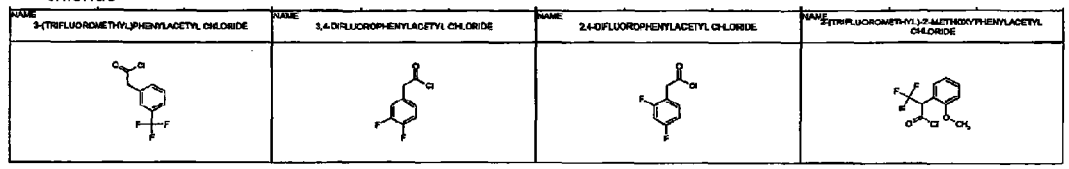

METHOD FOR INHIBITING *TRYPANOSOMA CRUZI*

RELATED APPLICATIONS

This application is a U.S. National Stage Application filed under 35 U.S.C. §371 of International Application PCT/US2012/048616, filed Jul. 27, 2012, designating the United States, which claims priority from U.S. Provisional Application 61/512,232, filed Jul. 27, 2011, the complete disclosures of which are incorporated herein by reference.

FIELD OF THE INVENTION

The present inventions relate to methods for inhibiting *Trypanosoma cruzi* using an imido-substituted 1,4-napthoquinone compound and certain novel imido-substituted 1,4-napthoquinones.

BACKGROUND OF THE INVENTION

Chagas disease is a vector-transmitted tropical disease caused by *Trypanosoma cruzi*.

Historically, Chagas disease has been regarded as largely affecting people living in rural areas of Latin America, primarily rural areas of Central and South America. The symptoms of the disease are silent and can appear many years after infection.

Chagas disease is expanding beyond its endemic area as a result of migration from and to the endemic countries (Hotez, 2008; Schofield and Kabayo, 2008). In addition, the World Health Organization (WHO) reports that blood donations and poor safety in blood banks have led to infections with Chagas disease in countries outside Latin America as some people who may be unaware they carry the infection have donated their blood to the national blood supply. As a result, the disease has now appeared in several countries in Europe and various parts of the United States of America.

A hematophagous insect (such as a triatomine insect) takes a blood meal from a vertebrate host infected with *Trypanosoma cruzi* and becomes a vector for Chagas disease. The insect ingests trypomastigotes from an infected vertebrate host, which proliferate and transform into the epimastigote form and then transform into the metacyclic trypmastigote form. The feces from the vector contain metacyclic trypomastigotes that can contaminate a bite or wound and pass into a vertebrate host (a mammalian "reservoir," which can be a human). The metacyclic trypomastigotes penetrate various cells at the bite or wound site and transform into amastigotes, which multiply by binary fission in cells of infected tissue. The intracellular amastigotes transform into trypomastigotes that then burst from the cells into the bloodstream. Clinical manifestations can result from the repetitive infective cycle in an infected vertebrate host.

Once an individual has contracted Chagas disease, the infection may remain relatively dormant, in some cases for decades. Many people who have the disease do not know they are infected. Chagas disease is a silent killer that causes the slow swelling of its victims' internal organs causing their eventual death. Most people later develop cardiac complications, resulting in disability and even death. Intestinal complications are also known to develop in patients resulting in an enlarged oesophagus or colon which make it difficult for the person to eat normally or pass stool.

There are currently two drugs used in the treatment of Chagas disease, benznidazole and nifurtimox. Where Chagas disease is endemic one of the two is used to treat disease victims. WHO has reported the two drugs (nifurtimox and benznidazole) are currently used to treat early stages of Chagas disease and that studies are being conducted for efficacy in treating later states of the disease. More recent literature reports the two drugs may be used to treat the acute phase of the infection where parasites (trypomastigotes) are detectable in the peripheral blood (Andrade et al., 2004; Schofield and Kabayo, 2008).

Nifurtimox is a 5-membered nitrofuran compound that is orally administered for 30 to 60 days. Benznidazole is an orally administered antiparasitic medication formerly marketed under the brand names Rochagan and Radanil. Benznidazole is reportedly effective in the acute or early chronic stage of infection with decreased effectiveness during late chronic phase. Recently, the emergence of *Trypanosoma cruzi* strains resistant to benznidazole have been reported. Both drugs have gastrointestinal and neurological side effects which may worsen as the patient ages. There are problems of non-compliance and there is no prescribed approved pediatric formulation.

Treatment is complicated due to high costs and side effects. Therapy mostly depends on the two known drugs developed decades ago that require long term administration, and are not available to all patients due to their high cost.

Consequently, there is a search for alternative drugs with efficacy against *Trypanosoma cruzi* and, in particular, drugs having a more selective mode of action. In the on-going search for alternatives, several classes of drug-like molecules have been considered. For instance, the naturally occurring lapachol (FIG. 1), and some of its derivatives reportedly show trypanocidal activity against *T. cruzi* (Salas et al., 2008). Use of naphthofuranquinones synthesized from 2-hydroxy-3-allyl-1,4-naphthoquinone against the epimastigote and trypomastigote forms of *T. cruzi* has been reported (Silva et al., 2006). A study involving 2,3-diphenyl-1,4-naphthoquinone against *T. cruzi* epimastigotes at a low micromolar concentration (LD50=2.5 µM) by inhibiting *T. cruzi* lipoamide dehydrogenase (TcLipDH) has been reported (Ramos et al., 2009). Still other efforts are focusing on other structurally diverse compounds, including other natural products (canthinones, catechin, hinokinin, as examples) and pyrimidine derivatives (fenarimol, as an example), and additional structurally diverse compounds. Other literature includes Menna-Barreto et al., 2009.

Despite a number of efforts, relating the structure and efficacy and selectivity of compounds for treating Chagas disease remains elusive and results can be unpredicatable.

In particular, there remains a need for appropriate chemotherapeutic treatment that can be used in *Trypanosoma cruzi*-infected patients, especially for slowing the progress of Chagas disease and for arresting development of severe forms of Chagas disease.

This situation establishes the unfulfilled need for new chemotherapeutic agents against *Trypanosoma cruzi*.

SUMMARY OF THE INVENTION

In its broadest aspect, a method for treating a mammalian patient at risk or suffering from a disease caused by a kinetoplastid parasite comprises administering to such subject an effective kinetoplasticidal amount of an imido-substituted 1,4-naphthoquinone to inhibit the kinetoplastid.

In an important aspect, a method of inhibiting *Trypanosoma cruzi* comprises administering to a patient for prophylaxis or to a patient in need of treatment an antitrypanosomal effective amount of an imido-substituted 1,4-naphthoquinone.

In another important aspect, a method of inhibiting *Trypanosoma cruzi* comprises administering to a patient for prophylaxis or to a patient in need of treatment an antitrypanosomal effective amount of an imido-substituted 1,4-naphthoquinone represented by the general formula:

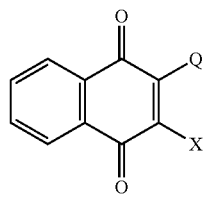

wherein X is alkyl, such as lower alkyl, alkoxy, benzyloxy aryloxy, trifluoro methyl, H, or halogen, as examples; and Q represents the imido-substituent bonded to the 1,4-napthoquinone moiety through the imido nitrogen.

In an aspect, a method of inhibiting tubulin polymerization in *Trypanosoma cruzi* in a patient in need of treatment comprises administering to the patient, in an amount effective for inhibiting tubulin polymerization, an imido-substituted 1,4-naphthoquinone represented by the above general formula.

In an aspect of the method, in the general formula, X is —$OR_1$ and $R_1$ is alkyl.

In an aspect of the method, in the general formula, X is —$OR_1$ (alkoxy) and $R_1$ is lower alkyl.

In an aspect of the method, when X is —OR, $R_1$ is cycloalkyl or a straight or branched alkyl, including for example $C_1$ to $C_{10}$ alkyl, preferably $C_1$ to $C_6$ alkyl.

In an aspect of the method, in the general formula, X is —$OR_1$ and $R_1$ is aryl.

In an aspect of the method, in the general formula, X is halogen.

In an aspect of the method, in the general formula X is bromo, chloro, fluoro or iodo.

In an aspect of the method, in the general formula, X is bromo or chloro.

In an aspect of the method, Q is represented by:

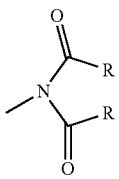

wherein in Q each R is, independently, a substituted or unsubstituted hydrocarbon, provided that one R can, optionally, be hydrogen, and provided that, optionally, R can include at least one hetero atom.

In an aspect of the method, Q is represented by:

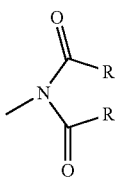

wherein in Q each R is, independently, cyclic or acyclic, substituted or unsubstituted, or the R groups in formula (1) bond together to form a cyclic imido-substituent.

In an aspect of the method, when Q is represented by:

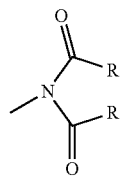

wherein each R is independent of the other, and
(a) R is an optionally substituted straight, branched or cyclic alkyl group, wherein the substitution is, for example, halogen, alkoxy or acetoxy,
(b) the R groups bond together to form an alkylene group whereby Q is a cyclic imido-substituent,
(c) the R groups bond together to form an alkylene group having a hetero atom, or
(d) R is aryl or substituted aryl, wherein the substitutent(s) include, for example, alkoxy or halogen.

When R is cycloalkyl or aryl, each ring can include 0, 1, 2, 3, 4, or 5 substituents. Each R is independent of the other. In principle, one R can be hydrogen.

In an aspect of the method, in an imido-substituted 1,4-naphthoquinone Q is an aryl-imido substituent.

In an aspect of the method, the imido-substituted 1,4-naphthoquinone in the general formula is represented by:

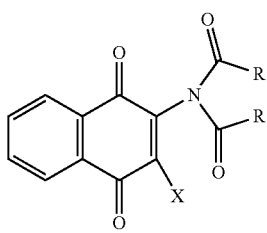

wherein each R is, independently, an optionally halo-substituted straight or branched $C_1$ to $C_{10}$ alkyl, preferably a $C_1$ to $C_6$ alkyl. X is alkyl, alkoxy (cyclic or alicyclic), trifluoro methyl, aryloxy, benzyloxy, hydrogen or halogen. X can be substituted alkyl or substituted alkoxy, aryloxy or benzyloxy.

In an aspect of the method, in an imido-substituted 1,4-naphthoquinone Q in the general formula is represented by:

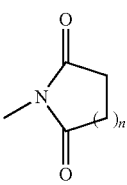

wherein the symbol ( ) designates —$(CH_2)$— and n is 1 to 3. Preferably n is 1 or 2.

In an aspect of the method, Q is represented by:

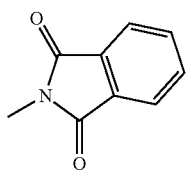

wherein the aryl ring may, optionally, be substituted, such as substituted with halogen.

In an aspect of the method, an imido-substituted 1,4-naphthoquinone is represented by:

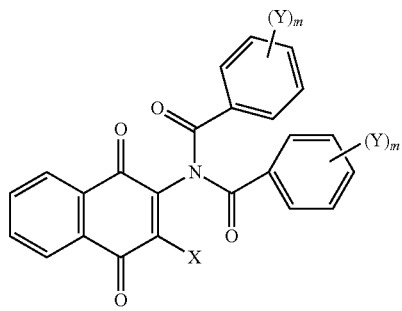

wherein X is hydrogen, halogen, alkoxy (cyclic or alicyclic), trifluoro methyl, aryloxy, or benzyloxy, to mention examples; each Y, independently, represents hydrogen, halogen, alkoxy (cyclic or alicyclic), trifluoro methyl or alkyl, and each m, independent of the other, is 0, 1, 2, 3, 4 or 5.

In an aspect of the method, on one of the aryl rings each Y can be hydrogen.

In an aspect of the method, when each m is 0, an imido-substituted 1,4-naphthoquinone is represented by:

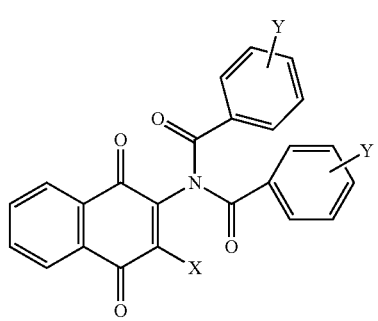

wherein each Y is hydrogen.

In an aspect of the method, an imido-substituted 1,4-naphthoquinone is represented by:

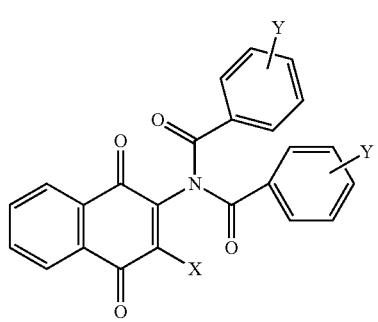

wherein X is hydrogen, halogen, alkoxy (cyclic or alicyclic), trifluoro methyl, aryloxy or benzyloxy, and each Y, independently, is alkoxy, aryloxy or halogen, and each m is 1. Y is ortho, meta or para-substituted. In another aspect, Y is meta-substituted. In a further aspect of this method, one Y can be hydrogen.

In an aspect of the method, an imido-substituted 1,4-naphthoquinone is represented by:

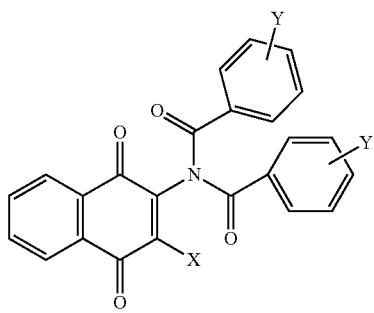

wherein X is hydrogen, halogen, alkoxy (cyclic or alicyclic), trifluoro methyl, aryloxy, or benzyloxy and each Y, independently, is halogen. X and Y are independent of each other. In a further aspect, Y is ortho, meta or para-substituted. In another aspect, Y is meta-substituted. In a further aspect of this method, one Y can be hydrogen.

In an aspect of the method, an imido-substituted 1,4-naphthoquinone having in vitro toxicity against *Trypanosoma cruzi* greater than nifurtimox is administered to a patient in need of treatment.

In an aspect of the method, an imido-substituted 1,4-naphthoquinone having a selectivity index against *Trypanosoma cruzi* greater than nifurtimox is administered to a patient in need of treatment.

In an aspect of the method, an imido-substituted 1,4-naphthoquinone having an $IC_{50}$ cytoxicity value greater than 100 µM is administered to a patient in need of treatment against *Trypanosoma cruzi*.

In an aspect of the method, an anti-trypanosomal effective amount of a compound selected from the group consisting of IMDNQ1, IMDNQ2, IMDNQ3, IMDNQ4, IMDNQ5, IMDNQ6, IMDQ7, IMDNQ8, IMDNQ9, IMNDQ10, and IMNDQ11 is administered to a patient to inhibit *Trypanosoma cruzi*.

In an aspect of the method, an anti-trypanosomal effective amount of a compound selected from the group consisting of IMDNQ1, IMDNQ 2, IMDNQ 3, and IMDNQ10 is administered to a patient.

In an aspect of the method, an anti-trypanosomal effective amount of IMDNQ10 is administered to a patient.

In an aspect, the method of inhibiting includes a method for treating a disease caused by *Trypanosoma cruzi*.

In an aspect, the method comprises treating a patient in need of treatment for Chagas disease with a therapeutically effective amount of an active ingredient that is a compound represented by the general formula.

In an aspect, the method comprises treating a patient in need of treatment for Chagas disease with a therapeutically effective amount of an active ingredient that is a compound selected from the group consisting of IMDNQ1, IMDNQ2, IMDNQ3, IMDNQ4, IMDNQ5, IMDNQ6, IMDQ7, IMDNQ8, IMDNQ9, IMNDQ10, and IMNDQ11.

In an aspect, the method comprises treating a patient in need of treatment for Chagas disease with a therapeutically effective amount of an active ingredient that is a compound selected from the group consisting of IMDNQ1, IMDNQ 2, IMDNQ 3, and IMDNQ10.

In an aspect, the method comprises treating a patient in need of treatment for Chagas disease by administering a therapeutically effective amount of an active ingredient that is IMDNQ10.

In an aspect, the method comprises prophylaxis against *Trypanosoma cruzi* by administering an effective anti-trypanosomal amount of a compound represented by general formula to a patient.

In an aspect, the method comprises prophylaxis against *Trypanosoma cruzi* by administering an effective anti-trypanosomal amount of an active ingredient that is a compound selected from the group consisting IMDNQ1, IMDNQ2, IMDNQ3, IMDNQ4, IMDNQ5, IMDNQ6, IMDQ7, IMDNQ8, IMDNQ9, IMNDQ10, and IMNDQ11.

In an aspect, the method comprises prophylaxis against *Trypanosoma cruzi* by administering an effective anti-trypanosomal amount of a compound selected from the group consisting of IMDNQ1, IMDNQ 2, IMDNQ 3, and IMDNQ10.

In an aspect, the method comprises prophylaxis against *Trypanosoma cruzi* by administering an effective anti-trypanosomal amount of a compound represented by of an active ingredient that is IMDNQ10 or a derivative thereof.

In an aspect, the method comprises inhibiting tublin polymerization in *Trypanosoma cruzi* by administering an effective anti-tublin polymerization amount of an imido-substituted 1,4-naphthoquinione compound. In a further aspect the compound is represented by the general formula.

DETAILED DESCRIPTION OF THE INVENTION

Figure 1:
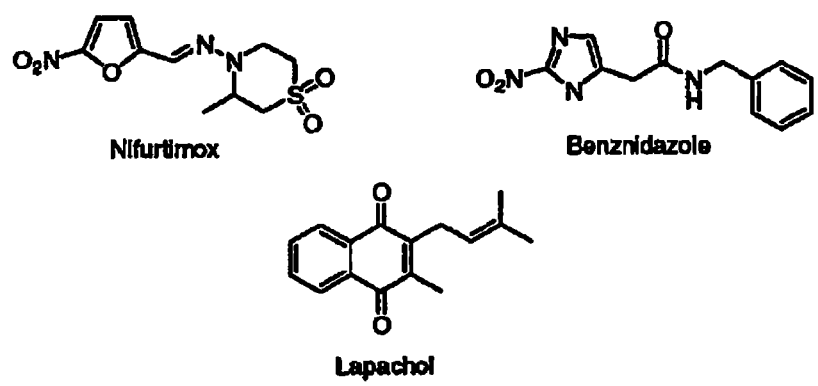
FIG. 1 shows the structures of nifurtimox, benznidazole and the naturally occurring lapachol.

The methods described herein advantageously utilize imido-substituted 1,4-naphthoquinones as a novel class of anti-trypanosomal agents to inhibit proliferation of *Trypanosoma cruzi*. The methods can provide prophylaxis or treatment for a vertebrate against *Trypanosoma cruzi*. The methods can provide treatment against the various stages of *Trypanosoma cruzi*. Thus, administering an imido-substituted 1,4-naphthoquinone can provide prophylaxis or treatment to a patient against the proliferation of *Trypanosoma cruzi*.

In particular, the method can provide treatment for a human against Chagas disease.

Administering an imido-substituted 1,4-naphthoquinone to a patient in a stage of infection with *Trypanosoma cruzi* can treat against metacyclic trypomastigotes.

Administering an imido-substituted 1,4-naphthoquinone to a patient in a stage of infection with *Trypanosoma cruzi* can treat against amastigotes.

Administering an imido-substituted 1,4-naphthoquinone to a patient in a stage of infection with *Trypanosoma cruzi* can treat against trypomastigotes that have burst from infected cells into the bloodstream.

Administering can be used to treat an acute phase of *Trypanosoma cruzi* infection where parasites (trypomastigotes) are detectable in the peripheral blood.

Administering for prophylaxis may help break the cycle of Chagas disease and reduce the patient's chances of becoming infected or infecting another through a vector.

Administering an imido-substituted 1,4-naphthoquinone to a patient can, in principle, lead to inhibiting proliferation of *Trypanosoma cruzi*, such as epimastigotes, in the disease vector. Once a vector ingests blood from the patient whose blood plasma contains a imido-substituted 1,4-naphthoquinone, further development of *Trypanosoma cruzi* in the vector may be inhibited.

The imido-substituted 1,4-naphthoquinones include 3-imido 2-alkoxy 1,4-napthoquinones, 3-imido 2-aryloxy 1,4-naphthoquinones, and 3-imido 2-halo-1,4-naphthoquinones.

An aspect of the method is inhibiting proliferation of *Trypanosoma cruzi* in a patient in need of treatment by administering an imido-substituted 1,4-naphthoquinone, especially a 3-imido 2-alkoxy 1,4-naphthoquinone, to the patient.

An aspect of the method is inhibiting proliferation of *Trypanosoma cruzi* in a patient in need of treatment by administering an imido-substituted 1,4-naphthoquinone, especially a 3-imido 2-aryloxy 1,4-naphthoquinone, to the patient.

An aspect of the method is inhibiting proliferation of *Trypanosoma cruzi* in a patient in need of treatment by administering an imido-substituted 1,4-naphthoquinone, especially a 3-imido-substituted 2-halo 1,4-naphthoquinone, to the patient.

An aspect of the method is inhibiting proliferation of *Trypanosoma cruzi* in a patient in need of treatment by administering a cyclic-imido-substituted 1,4-naphthoquinone, to the patient.

An aspect of the method is inhibiting proliferation of *Trypanosoma cruzi* in a patient in need of treatment by administering an acyclic-imido-substituted 1,4-naphthoquinone, to the patient.

Administering includes sublingual administration, oral administration, and, in principle, intravenous administration. A pharmaceutical composition can contain the active pharmaceutical ingredient and may additionally comprise a pharmaceutically acceptable vehicle or adjuvant. A pharmaceutical composition can be in the form of a solid pharmaceutical dosage form (tablet, caplet, capsule, or deliverable from an osmotic pump as examples) or syrup. Remington, The Science and Practice of Pharmacy, provides general information regarding pharmaceutical dosage forms.

An anti-trypanosomal effective amount of the imido-substituted 1,4 naphthoquinone refers to an amount effective in inhibiting proliferation of *Trypanosoma cruzi* and includes an trypanocidal amount against *Trypanosoma cruzi*.

A therapeutically effective amount means an amount of the imido 1,4-naphthoquinone that can provide a therapeutic benefit to a patient against *Trypanosoma cruzi*.

Patient includes human. A patient in need of treatment includes a human patient in need of treatment against *Trypanosoma cruzi*. Thus, methods of treating a mammal other than human (veterinary treatments) against *Trypanosoma cruzi* are also within the scope of our inventions.

Figure 3:
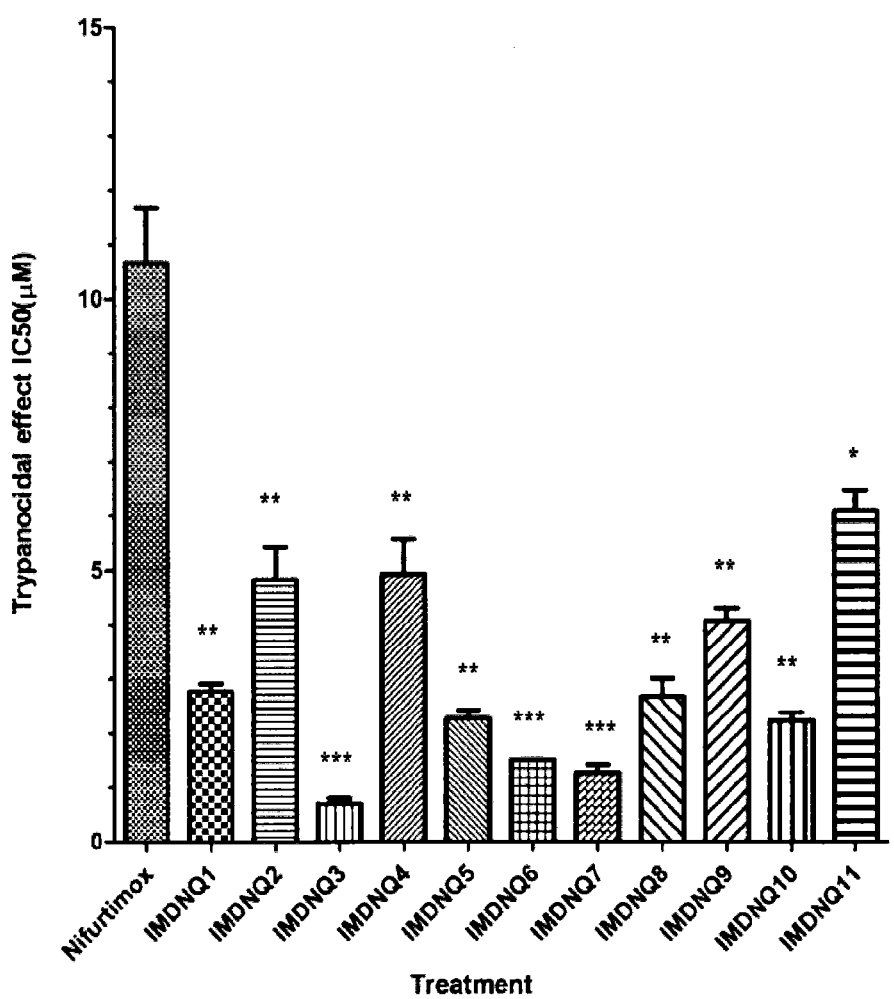
FIG. 3 is a bar graph showing the trypanocidal effects of certain imido-substituted 1,4-naphthoquinones on *Trypanosoma cruzi*. Results were expressed as means±S.E. of three experiments. *$P<0.05$, $P<0.01$, *$P<0.001$ compared with Nifurtimox.

A method for inhibiting proliferation of *Trypanosoma cruzi* with imido-substituted 1,4-naphthoquinones, such as imido-substituted 2-halo 1,4-napthoquinones, can exhibit greater antitrypanosomal efficacy against *Trypanosoma cruzi* than the presently clinically used nifurtimox. For example, compared to nifurtimox ($IC_{50}$=10.67 μM), representative imido-naphthoquinone analogs (IMDNQ1-IMDNQ11, as examples) are significantly more potent against *Trypanosoma cruzi* with $IC_{50}$ values ranging from 0.7 μM to 6.1 μM (P<0.05, FIG. 3). Thus, in one of its aspects the method for inhibiting proliferation of *Trypanosoma cruzi* comprises administering an imido-substituted 1,4-napthoquinone, such as an imido-substituted 2-halo 1,4-napthoquinone, having an acceptable $IC_{50}$ value, preferably an $IC_{50}$ value equal to or better than nifurtimox.

A method for inhibiting proliferation of *Trypanosoma cruzi* with an imido-substituted 1,4-naphthoquinone, especially an imido-substituted 2-halo 1,4-napthoquinone, can exhibit greater selectivity against *Trypanosoma cruzi* than the presently clinically used nifurtimox. The representative compounds IMDNQ 1-11 described herein are significantly more selective in inhibiting the parasite's growth than nifurtimox. For example, representative imido-naphthoquinone analogs (IMDNQ1, IMDNQ2, IMDNQ3 and IMDNQ10, as examples) unexpectedly significantly exhibited in vitro selectivity indices of at least about 300% greater than nifurtimox. Thus, in another of its aspects the method for inhibiting proliferation of *Trypanosoma cruzi* comprises administering an imido-substituted 1,4-naphthoquinone, such as an imido-substituted 2-halo 1,4-napthoquinone, having an acceptable selectivity index, preferably a selectivity index better than nifurtimox.

Figure 4:
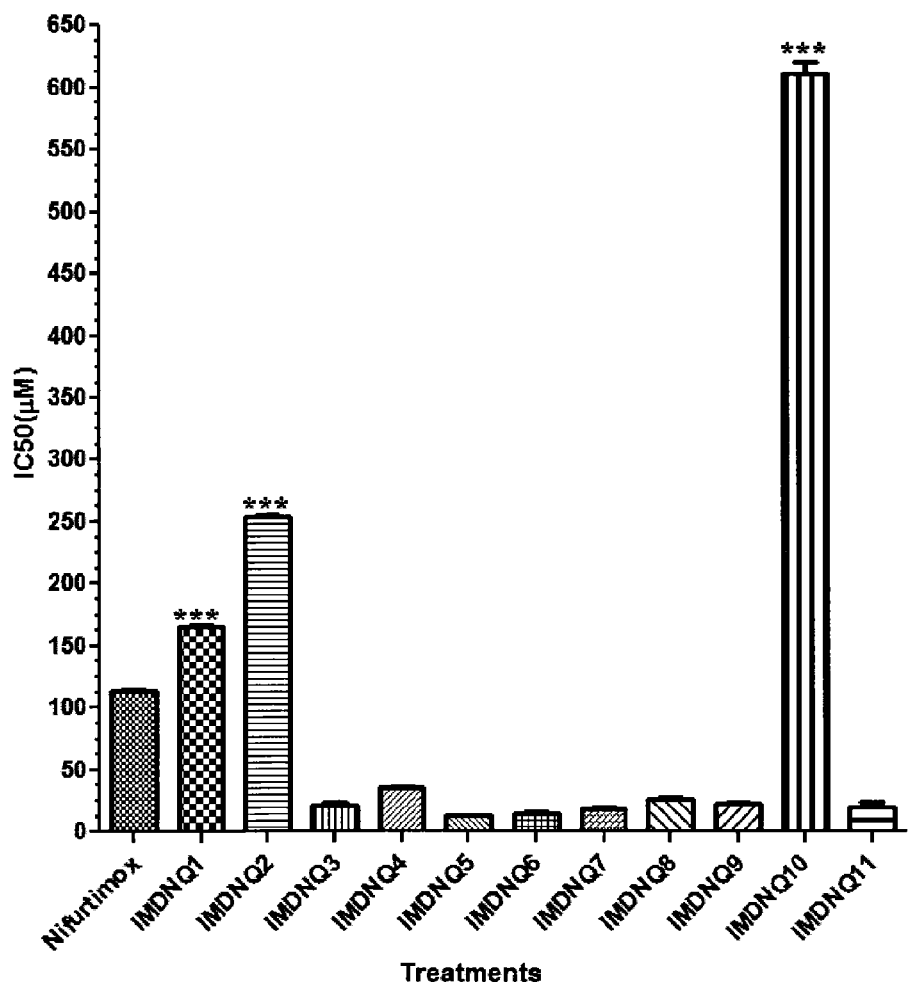
FIG. 4 is bar graph showing the cytotoxicity of certain imido-substituted 1,4-naphthoquinones on Balb/C 3T3 mouse fibroblasts. Results were expressed as means±S.E. of three experiments. ***$P<0.0001$ compared with Nifurtimox.

A method for inhibiting proliferation of *Trypanosoma cruzi* with an imido-substituted 1,4-naphthoquinone, such as an imido-substituted 2-halo 1,4-napthoquinone, can exhibit good cytotoxicity characteristics. In vitro testing has demonstrated representative imido-naphthoquinone analogs were relatively non-cytotoxic to Balb/C 3T3 mouse fibroblast cell line with $IC_{50}$ values of well over 100 μM. For example, cytotoxicity study on Balb/C 3T3 mouse fibroblast cell line showed that IMDNQ1, IMDNQ2, and IMDNQ10 are far less cytotoxic than nifurtimox (FIG. 4). Thus, in yet another of its aspects the method for inhibiting proliferation of *Trypanosoma cruzi* comprises administering an imido-substituted 1,4-naphthoquinone, such as an imido-substituted 2-halo 1,4-napthoquinone, having an acceptable cytotoxicity value, preferably a value better than nifurtimox.

In the synthesis of the imido-substituted 1,4-naphthoquiniones, compounds represented by the formula:

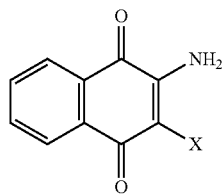

wherein X is hydrogen, halogen, alkoxy (cyclic or alicyclic), trifluoro methyl, benzyloxy or aryloxy are suitable starting materials that provide the 1,4-napthoquinone skeleton. For example, a 2-amino-3-halo-1,4-naphthoquinone is a suitable starting material for preparing imido-substituted 1,4, naphthoquiones having a 2-halo 1,4-naphthoquinone skeleton. The 2-amino-3-chloro-1,4-naphthoquinone is commercially available. It can also be facilely obtained from 2,3-dichloro-1,4-naphthoquinone and ammonia in a mixture of concentrated ammonium hydroxide and ethanol. A 2-amino-3-bromo-1,4-naphthoquinone starting material can be prepared by refluxing commercially available 2,3-dibromo-1,4-naphthoquinone with ammonia/ammonium hydroxide mixture in ethanol. A 2-amino-3-iodo-1,4-naphthoquinone starting material can be prepared as described in Perez et al., Synthesis of Iodinated Naphthoquinones Using Morpholine-Iodine Complex, Synthetic Communications, 34(18):3389-3397 (2004) (compound (4)), the complete disclosure of which is incorporated herein by reference. For imido-substituted 1,4, naphthoquiones having a 2-alkoxy 1,4-naphthoquinone skeleton, a 2-amino-3-alkoxy-1,4-naphthoquinone or 2-amino 3-aryloxy-1,4-naphthoquinone are representative classes of starting material. Synthesis includes Examples 12-13. It will be appreciated that X can also be halo-alkyl, such as trifluoro methyl, or halo-alkoxy, such as trifluoromethoxy.

A starting material where X is alkoxy or aryloxy can be synthesized by adapting procedures in Examples 12 and 13. In Example 12, a 2,3-dichloro 1,4-naphthoquinone is used as a representative 2,3-dihalo 1,4-napthoquinone in the synthesis of 2,3-dimethoxy-1,4-naphthoquinone. In Example 12, NaOMe is used as a representative reactant. When X is another alkoxy, aryloxy or benzyloxy, to mention examples, another suitable starting material is selected instead of NaOMe. Examples 14-19 describe 2-imido-substituted 3-methoxy 1,4-naphthoquinone compounds and it will be appreciated that X is not limited to methoxy when X is alkoxy.

X can be alkoxy or aryloxy, and is represented by $-OR_1$ where $R_1$ represents alkyl or aryl. $R_1$ represents straight or branched chain alkyl or cycloalkyl. X can be methoxy, ethoxy, propyloxy, butoxy, pentoxy, and hexyloxy, as examples. When X is cycloalkoxy, $R_1$ can be cyclopentyl or cyclo hexyl as examples. X can be branched alkoxy when $R_1$ is a branched alkyl such as isopropyl, isobutyl, t-butyl, isohexyl or isoamyl, as examples. X can be aryloxy in the general formula. X can be benzyloxy. X can also be a substituted alkoxy group, such as trifluoro alkoxy (trifluoro methoxy is an example), or a halo-alkyl, such as trifluoro methyl as an example.

The above-mentioned starting materials are suitable for reacting with a selected acid halide(s) to obtain the imido-substituted 1,4-naphthoquinone compound. Exemplary acid halides are shown in FIG. 6.

In the following description, the imido substituent may be shown as being 'symmetrical' for illustrative purposes and it should be understood that the imido substitutent can be mixed. For example, in a "mixed" imido compound useful in the present methods, the "R" groups in the imido substitutent can be the same or different, and each Y can be the same or different, in which case an "unsymmetrical" or mixed imido substituent is provided.

In the following description, various syntheses and compounds are shown in which X is chloro. It will be appreciated that X is not restricted to chloro. X can be a halogen other than chloro, alkyl, substituted alkyl, alkoxy, substituted alkoxy, aryloxy substituted aryloxy, benzyloxy, or substituted benzyloxy, to mention examples.

In an aspect of the method, Q is represented by:

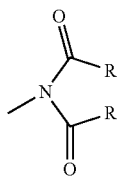

wherein in Q each R is, independently, a substituted or unsubstituted hydrocarbon, provided that one R can, optionally, be hydrogen, and provided that, optionally, R can include at least one hetero atom.

A sub-class of imido-substituted 1,4-naphthoquinones includes those represented by the formula:

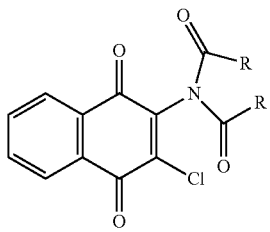

In general, each R is independently a cyclic or acyclic group. Each R includes acyclic, such as straight chain alkyl —$(CH_2)_nCH_3$) or branched alkyl, or cyclic, such as cyclo alkyl, or aryl. The expression open-chain imide derivative connotes the case where R is straight or branched alkyl. In another aspect, R can include unsaturation, e.g, an alkenyl. R can be cyclo alkyl, which includes cyclopropyl, cyclobutyl, cyclopentyl, cyclohexyl and the like. By preference, cyclo alkyl is a $C_5$ to $C_7$ cyclo alkyl. The R groups may be bonded to each other to form an alkylene bridge, such as a divalent alkylene bridge, although it will be appreciated that the R groups can, together, comprise a polycyclic moiety.

Depending on the R group, the imido compounds can adapt an anti-conformation. For instance, when R is acyclic, the acyclic imido groups can adapt anti-orientation or are capable of some form of staggered orientation, whereas when R is cyclic, the imido groups tend to adapt the syn orientation.

Compounds represented by the foregoing formula can be synthesized by adapting the following representative reaction scheme:

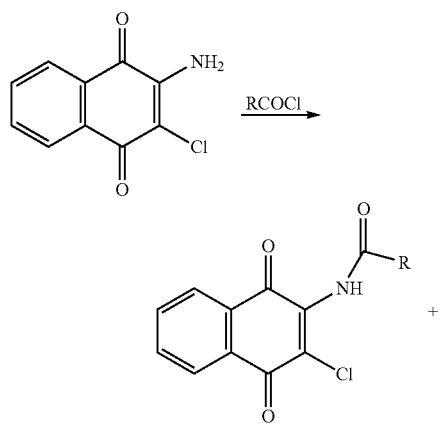

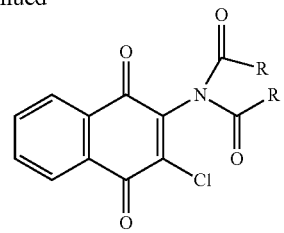

wherein RCOCl is selected to provide the desired R group, and purification of the reaction product yields the intended compound(s) within the general formula for the imido-substituted 1,4-naphthoquinone. Although X is chloro in the example, it will be appreciated that by selecting the appropriate starting material, X can be, for instance, another substituent.

When R is a straight chain alkyl —$(CH_2)_nCH_3$, n is generally 0 to 10, preferably 2 to 5, including methyl, ethyl, propyl, butyl, pentyl, and hexyl, such as

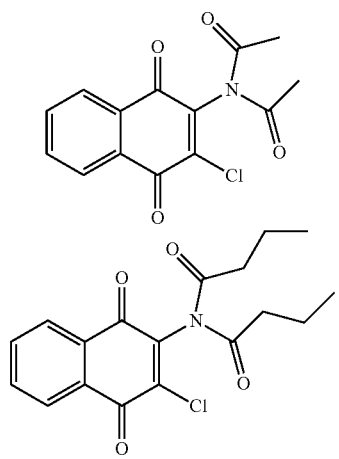

as examples. Longer R groups are possible. Although X is chloro in the example, it will be appreciated that by selecting the appropriate starting material, X can be, for instance, another substituent.

When R is branched the branching can be along the chain or can be terminal branching. For terminal branching, an R group can be represented by —$(CH_2)_nCH(CH_3)_2$ as an example, where n is from 0 to 6, preferably from 1 to 4, such as

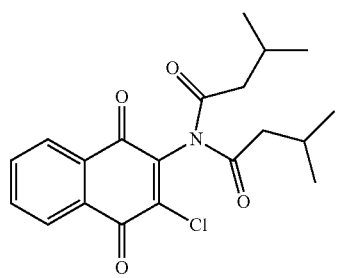 [SMILES: CC(C)CC(=O)N(C(=O)CC(C)C)C1=C(Cl)C(=O)c2ccccc2C1=O]

as an example. Although X is chloro in the example, it will be appreciated that by selecting the appropriate starting material, X can be, for instance, another substituent.

Within the foregoing sub-classes of the above imido-substituted 1,4-naphthoquinones are those in which the open chain imido derivatives have halogen substitution. In one aspect, in a halo-substituted alkylene derivative according to formula (1), the R groups have terminal halo-substitution, such as IMDNQ11. Suitable compounds can be synthesized as shown in the following representative exemplary reaction scheme:

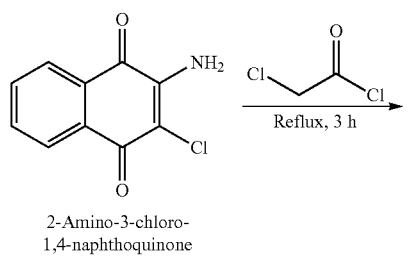

2-Amino-3-chloro-
1,4-naphthoquinone

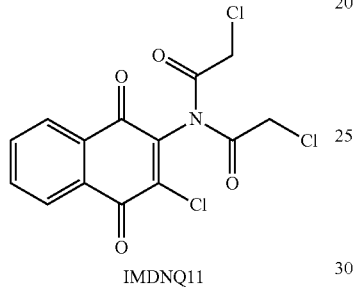

IMDNQ11

An exemplary chloroacyl chloride reagent is shown for illustrative purposes. Other suitable reagents, such as another acyl dihalide can be selected so that the alkyl group has different halo-substitution, such as a terminally bromo-substituted alkyl group (such as by using bromoacetyl bromide). Monohalogenation is illustrated but it will be appreciated that other multi-halogenated derivatives are included within the scope of the present methods. Other suitable acyl halides include 2-bromopropionyl chloride, 2-chloropropionyl chloride, 2,3-dibromopropionyl chloride, 2,3-dichloropropionyl chloride, bromoacetyl chloride, 3-bromopropionyl chloride, 4-chloropropionyl chloride, 4-bromopropionyl chloride, 4-bromobutryl chloride, 4-chlorobutryl chloride, 2,4-dibromobutryl chloride, 5-chlorovaleroyl chloride, 5-bromovaleroyl chloride, dichloroacetyl chloride, trichloroacetyl chloride, 6-chloroheanoyl chloride, as the like by as examples. Although X is chloro in the example, it will be appreciated that by selecting the appropriate starting material, X can be, for instance, another substituent.

The R groups can also be bonded together to form an alkylene bridge —(CH2)$_n$- in which case n is an integer of 1 to 3, preferably n is 2 or 3, so that Q represents a cyclic imido-substitutent (a nitrogen-containing ring having dione substitution) such as

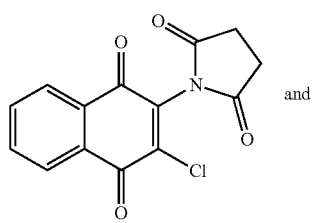

and

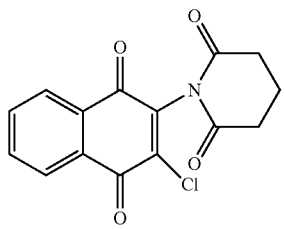

to mention examples. The 3-cyclic-imido-substituted 2-halo 1,4-napthoquinone compounds can be synthesized by adapting the following representative reaction scheme:

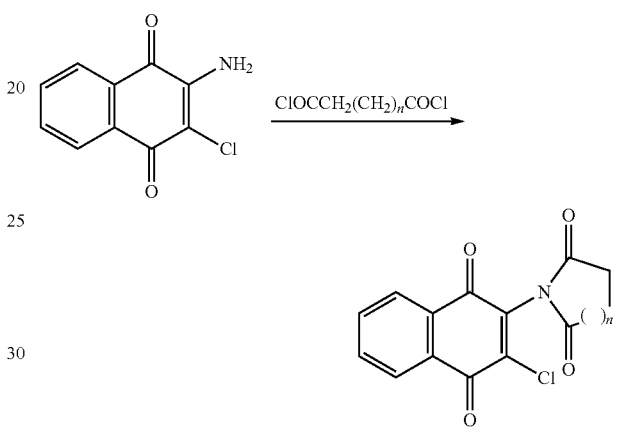

wherein ( ) designates —(CH$_2$)— and n is an integer of 1 to 3. 2-chloro-3-(N-succinimidyl)-1,4-naphthoquinone is obtained when n is 1. As shown, the succinimidyl derivative (IMDNQ1) has a surprisingly beneficial combination of properties. 2-chloro-3-(N-glutaimidyl)-1,4-napthoquinone is obtained when n is 2. Although X is shown as chloro in the exemplary formulas and in the representative synthesis, it will be appreciated that by selecting the appropriate starting material, X can be, for instance, another substitutent.

A further sub-class of 2-imido-substituted 1,4-naphthoquinones includes derivatives in which the 2-imido-substitution comprises a heterocyclic ring having dione substitution in which the additional hetero atom is preferably oxygen. For instance, the ring can be a five or six member ring with oxygen as an additional hetero atom. An exemplary derivative is a morpholine dione analog, such as IMDNQ4. Morpholine dione analogs can be synthesized as shown in the following exemplary reaction scheme:

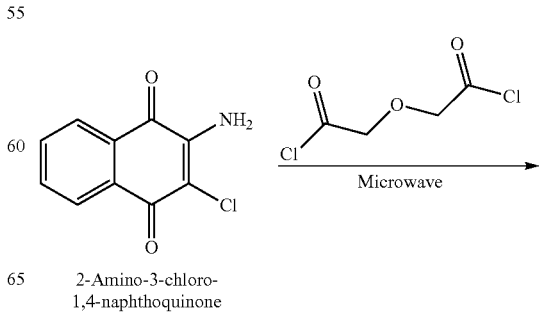

2-Amino-3-chloro-
1,4-naphthoquinone

-continued

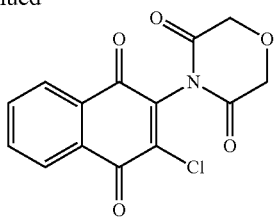

X is not restricted to chloro. X can be another halogen, alkoxy, aryloxy or benzyloxy, to mention examples. When X is halogen, the microwave treatment can vary in duration and intensity, as seen from Berhe, S., et al., Microwave-assisted synthesis of imido-substituted 2-chloro-1,4-naphthoquinone derivatives and their cytotoxic activities on three human prostate cancer cell lines, *Lett. Drug Des. Discov.*, 5, 485-488 (2008), but typically on lab scale synthesis the duration is on the order of minutes.

A sub-class of imido-substituted 1,4-naphthoquinones includes phthalimidyl derivatives. The compound IMDNQ2 is an example.

A sub-class of imido-substituted 1,4-naphthoquinones includes the cyclic imido-substituted derivatives, which include diarylimido-substituted derivatives. Diarylimido-substituted derivatives, which may be optionally substituted, include those represented by the formula:

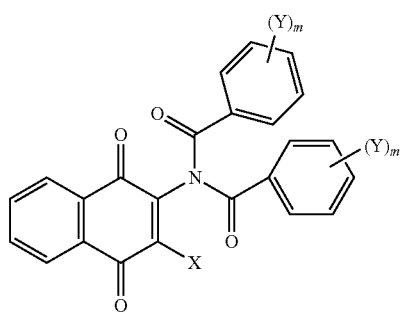

wherein X is halogen, hydrogen, alkyl, substituted alkyl, alkoxy (cyclic or alicyclic), trifluoro methyl, substituted alkoxy, aryloxy, substituted aryloxy, benzyloxy, or substituted benzyloxy, as examples; each Y, independently, is hydrogen, halogen, alkoxy, alkyl, halo-alkyl, or halo-alkoxy and m is 0, 1, 2, 4, or 5 or 3. When an m=0, Y is hydrogen. X and Y are independent of each other.

Exemplary diarylimido derivatives having Y halogen substitution include those when m is 1 represented by the formula:

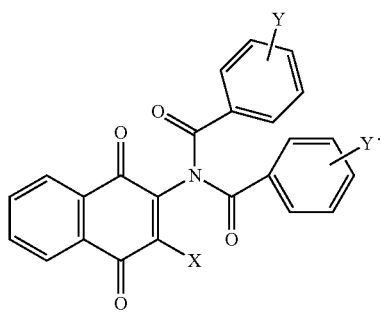

Examples include those compounds denoted herein as IMDNQ5 through IMDNQ10.

Mono-halogen-substituted diarylimido derivatives can be synthesized as shown in the following exemplary reaction scheme:

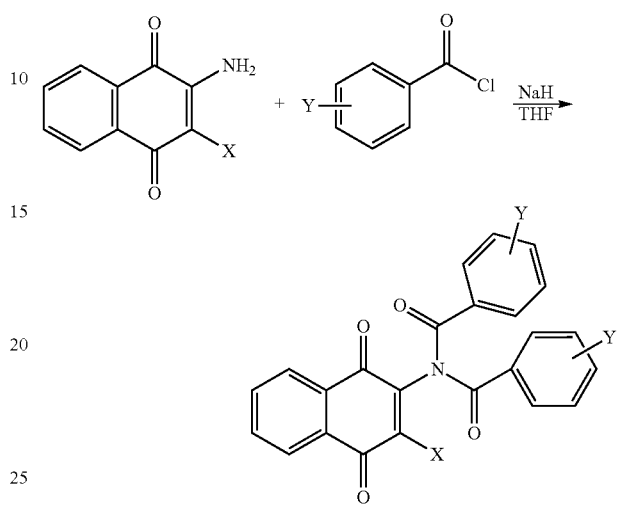

In the exemplary reaction scheme, X is halogen, hydrogen, alkyl, substituted alkyl, alkoxy (cyclic or alicyclic), trifluoro methyl, substituted alkoxy, aryloxy, substituted aryloxy, benzyloxy, or substituted benzyloxy, as examples; and each Y, independently, is H, halogen, alkyl or alkoxy. Co-produced is a mixed imido compound having R hydrogen and the other R is an aryl-imido substituent. X includes bromo, chloro, fluoro, and iodo. Bromo, chloro and fluoro may be preferred when X is halogen. Y may be at the meta, ortho and/or para position of the aryl ring. Meta-halogen substitution on each aryl ring in the imido moiety may be preferred when Y is halogen. Y includes bromo, chloro, fluoro, and iodo. More particularly, Y can be bromo, chloro or fluoro. When Y is a halogen, Y may preferably be chloro or fluoro, with chloro being preferred. IMDNQ10 is a member of this sub-class of imido-substituted 1,4-naphthoquinones. Y can be alkyl, including branched alkyl, or alkoxy as shown in the Examples. When Y is hydrogen, benzoyl chloride can be used.

In general, for the compounds in which an arylimido group is (are) substituted with one or more Y substituent, a synthesis, such as a synthesis above or in the Examples, can be adapted and

may be used where m is 1, 2, 3, 4 or 5. Acyl halides include 3,5-bis(trifluoromethyl)benzoyl chloride, 2-bromobenzoyl chloride, 2-chlorobenzoyl chloride, 2-fluorobenzoyl chloride, 2-iodobenzoyl chloride, 2-methoxybenzoyl chloride, 2-ethoxybenzoyl chloride, 2-(trifluoromethoxy)benzoyl chloride, 2,4-difluorobenzoyl chloride, 2,6-difluorobenzoyl chloride, 2,4-dichlorobenzoyl chloride, 2,6-dichlorobenzyol chloride, O-acetylsalicyloyl chloride, 2-methoxybenzoyl chloride, 2,6-dimethoxybenzoyl chloride, 2-(trifluoromethyl)benzoyl chloride, 3-bromobenzoyl chloride, 3-chlorobenzoyl chloride, 3-fluorobenzoyl chloride, 3-iodobenzoyl chloride, 3,4-bromobenzoyl chloride, 3,4-di-chlorobenzoyl chloride, 3-methoxybenzoyl chloride, 3,4-dimethoxybenzoyl chloride, 3,4-dimethylbenzoyl chloride, 3,4-difluorobenzoyl chloride, 3,4,5-trimethoxybenzoyl chloride, 3-(trifluoro)benzoyl chloride, 3-(chloromethyl)benzoyl chloride, 4-bromobenzoyl chloride, 4-chlorobenzoyl chloride, 4-fluorobenzoyl chloride, 4-iodobenzoyl chloride, 4-methoxybenzoyl chloride, 4-ethoxybenzoyl chloride, 4-butoxybenzoyl chloride, 4-(hexyloxy)benzoyl chloride, 4-(heptyloxy)benzoyl chloride, 4-(trifluoromethyl)benzoyl chloride, 4-(tert-butyl)benzoyl chloride, 4-(trifluoromethoxy)benzoyl chloride, 4-ethoxybenzoyl chloride, 4-propylbenzoyl chloride, 4-butylbenzoyl chloride, 5-pentylbenzoyl chloride, 4-hexylbenzoyl chloride, 4-heptylbenzoyl chloride, 3,5-dichlorobenzoyl chloride, 2,3-dichlorobenzoyl chloride, 2,3-difluorobenzoyl chloride, 2,5-dichlorobenzoyl chloride, 2,5-difluorobenzoyl chloride, 3,5-dimethoxybenzoyl chloride, 2,4,6-trimethylbenzoyl chloride, 2,4,6,-trichlorobenzoyl chloride, 2,4,6,-trifluorobenzoyl chloride, 2,4,5-trifluorobenzoyl chloride, 2,3,4-trifluorobenzoyl chloride, 2,4-dimethoxybenzoyl chloride, 2,5-dimethoxybenzoyl chloride, 2-fluoro-3-(trifluoromethyl)benzoyl chloride, 2-fluoro-4-(trifluoromethyl)benzoyl chloride, 2-fluoro-5-(trifluoromethyl)benzoyl chloride, 3-fluoro-5-(trifluoromethyl)benzoyl chloride, 4-fluoro-2-(trifluoromethyl)benzoyl chloride, 4-fluoro-3-(trifluoromethyl)benzoyl chloride, 5-fluoro-2-(trifluoromethyl)benzoyl chloride, 2-fluoro-6-(trifluoromethyl)benzoyl chloride, 2,4-bis(trifluoromethyl)benzoyl chloride, 2,6-bis(trifluoromethyl)benzoyl chloride, 3-(trifluoromethoxy)benzoyl chloride, 2,3,4,5-fluorobenzoyl chloride, 2,4-dichloro-5-fluorobenzoyl chloride, 3-(dichloromethyl)benzoyl chloride, 2,3,5-trifluorobenzoyl chloride, 3,4,5-trifluorobenzoyl chloride, 2-chloro-6-fluorobenzoyl chloride, 3-chloro-4-fluorobenzoyl chloride, 4-chloro-2,5-difluorobenzoyl chloride, 5-fluoro-2-methylbenzoyl chloride, 3-fluoro-4-methylbenzoyl chloride, 2,6-difluoro-3-methylbenzoyl chloride, 3-chloro-2-6-(trifluoromethyl)benzoyl chloride, 5-chloro-2-(trifluoromethyl)benzoyl chloride, and 2-chloro-6-fluoro-3-methylbenzoyl chloride, 6-chloro-2fluoro-3-methylbenzoyl chloride, 2-chloro-5-fluorobenzoyl chloride, 4-fluoro-3-methyl chloride, 5-chloro-2-fluorobenzoyl chloride, 2-chloro-3,6-fluorobenzoyl chloride, 3-chloro-2,4-fluorobenzoyl chloride, 3-chloro-2-fluoro-5(trifluoromethyl)benzoyl chloride, 4-methoxy-3-(trifluoromethyl) benzoyl chloride, 4-methyl3-(trifluoromethyl)benzoyl chloride, 2-chloro-5-(trifluoromethyl)benzoyl chloride, 2,3-difluoro-4-methylbenzoyl chloride, 3,5-dichloro-4-methoxybenzoyl chloride, 2,4,5-trifluoro-3-methoxybenzoyl chloride, 2,3,4,6-tetrafluorobenzoyl chloride, 5-bromo-2,3,4-trimethylbenzoyl chloride, 4-bromo-2,6-difluorobenzoyl chloride, 2-fluoro-5-iodobenzoyl chloride, 2-fluoro-6-iodobenzoyl chloride, 4-bromo-2-fluorobenzoyl chloride, and 2-bromo-6-chlorobenzoyl chloride by way of example.

Other imido-substituted 1,4-naphthoquinones with different Q moieties can be obtained with other acid halides, including those disclosed in FIG. 6, such as, for example, O-acetylmandelic chloride, phenoxyacetyl chloride, 4-chlorophenoxyacetyl chloride, phenylacetyl chloride, cinnamoyl chloride, hydrocinnamoyl chloride, 2-chloro-2,2diphenylacetyl chloride, alpha-chlorophenylacetyl chloride, 1-napthoyl chloride, 2-napthoyl chloride, 3,4(dimethoxy)benzoylacetyl chloride, 3-methoxyphenylacetyl chloride, 3-phenoxyproprionyl chloride, 2-(1-naphthyl)ethanoyl chloride, and 2-(3,5-difluorophenyl)ethanoyl chloride, 2-bromophenylacetyl chloride, 3-acetoxy-2-methylbenzoyl chloride, by way of alternative aryl groups. It will thus be appreciated that when an R group is aryl or aryloxy or cyclo alkyl (which includes polycyclic alkyl), there may be an intervening linking group (sometimes called a spacer group) between the aryl or aryloxy or cyclo alkyl group to the imido-functional group. An exemplary such linking group would be an alkylene group, as an example.

In each of the various aspects of the present inventions, a Y substituent can be substituted alkyl, such as halogen-substituted alkyl, including trifluoro methyl, or substituted alkoxy, such as halogen-substituted alkoxy, including trifluoromethoxy, to mention examples.

The imido-substituted 1,4-naphthoquinone compound can be symmetrical or mixed, such as shown in the Examples. An exemplary reaction scheme for preparing a sub-class of imido-substituted 1,4-naphthoquinones having mixed Y group(s) can be represented as follows:

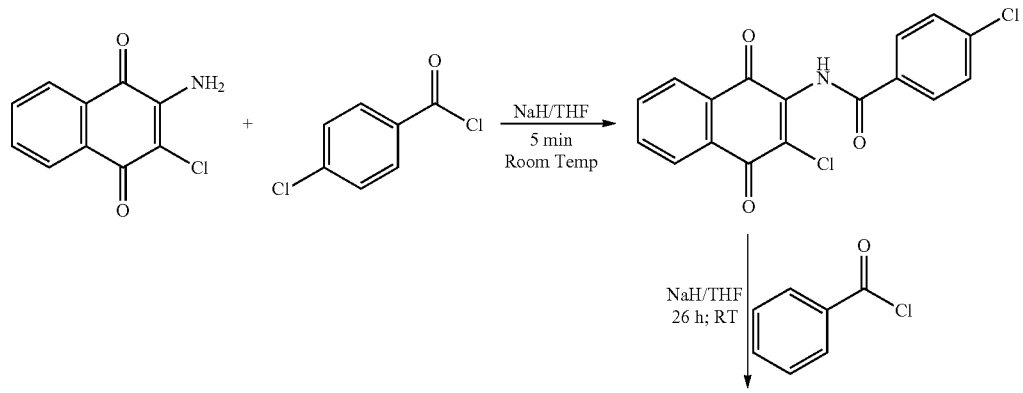

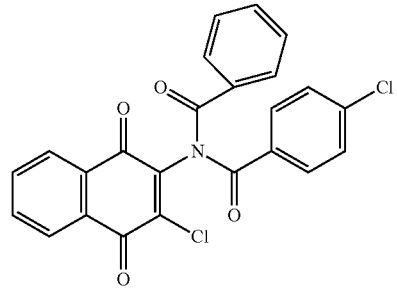

It will be appreciated that an unsymmetrical imido substituent, e.g., "mixed" as to an aryl ring(s), the Y substituent(s), and/or in the position(s) of a Y substituent(s) may be achieved by selecting a desired member from the class of acid chlorides from the class of benzoyl chlorides for the first step, and a different member for the second step. It will also be appreciated that a "mixed" imido-substituted 1,4-naphthoquinone is obtained in the first step wherein, for instance, the imido-nitrogen is bonded to hydrogen (one of the R groups) and the other R is substituted aryl. Other "mixed" compounds are obtained by adapting an appropriate synthesis and using an appropriate acid halide, which includes the exemplary acid chlorides in FIG. 6. For instance, other "mixed" imido-substituted 1,4-naphthoquinione compounds include an R being other than hydrogen and the other R being a different substituted or unsubstituted hydrocarbon.

Another sub-class of imido-substituted 1,4-naphthoquinones have unsymmetrical substitution with alkyl and aryl in the imido moiety (Q group), and can be synthesized by adapting the following representative reaction scheme. An aminonaphthoquinone analog is first converted to the alkyl amido derivative which is subsequently reacted with an aryl acid chloride in the presence of an alkali hydride, such as sodium hydride, in anhydrous THF to furnish the imido-substituted 1,4-naphthoquinone derivative having Unsymmetrical substitution with alkyl and aryl in the imido moiety:

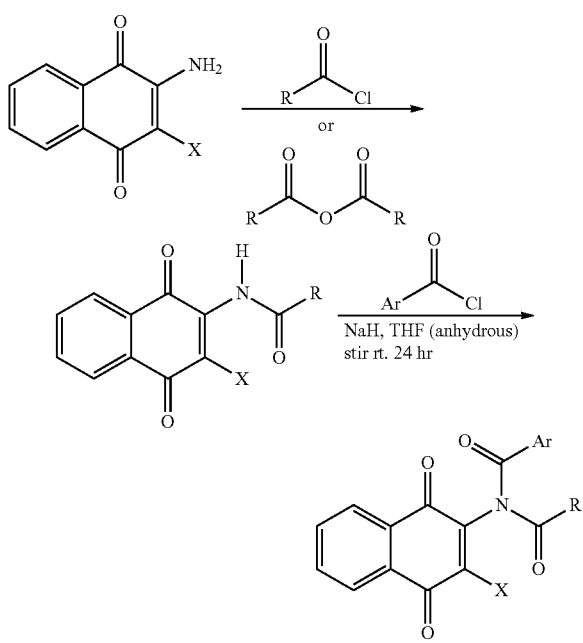

An R group can be alkyl, such as described elsewhere herein, which includes $C_1$-$C_6$ alkyl. The other R group can be an aromatic group, such as an aryl group, such as described elsewhere herein. X can be a substitutent as described elsewhere herein, which includes, for example, hydrogen, halogen, akyl, alkoxy (such as lower alkoxy, methoxy or the like).

A 1,4-naphthoquinone starting material as shown in various reaction schemes herein is chloro substituted (X=chloro) only for illustrative purposes. It will be appreciated that the 1,4-naphthoquinone starting material can have a 2-substitution so that X in the general formula and in the various formulas can be other than chloro.

Figure 2:
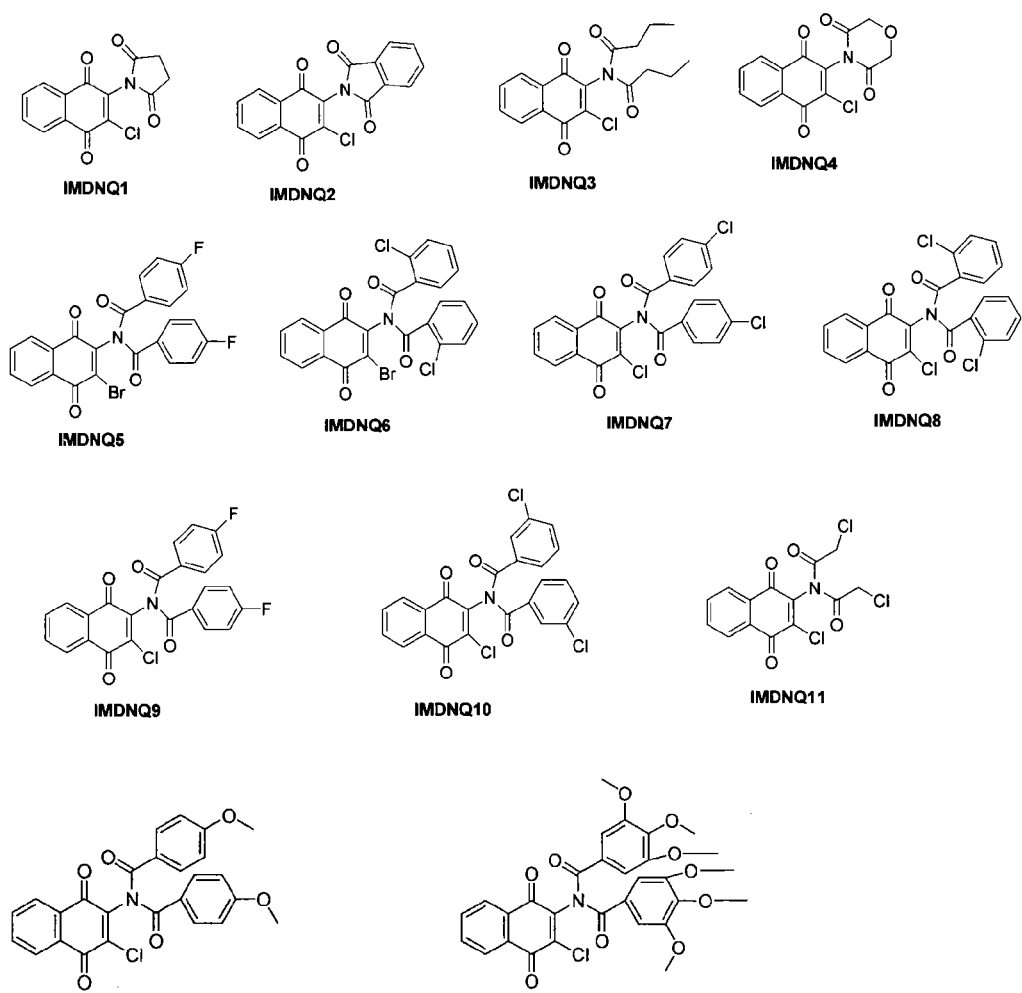
FIG. 2 shows the structures for the imido-substituted 1,4-naphthoquinones according to Examples 1-29.

In the general formula for the imido-substituted 1,4-naphthoquinones, the selection of X as halogen may not drastically affect activity and selectivity towards *Trypanosoma cruzi* in compounds as seen from Examples 1-11. For example, it appears that when X is bromo instead of X is chloro on the 1,4-naphthoquinone ring may not drastically affect the activities and selectivity indices of the compounds according to Examples 1-11. This is shown by the activity and selectivity of compound IMDNQ6 versus IMDNQ8, and also compound IMDNQ5 versus IMDNQ9 (Table 1, FIG. 2). A slight increase in antitrypanosomal activity against *Trypanosoma cruzi* may arise when the 3-chloro-group is substituted with a 3-bromo group as seen in compounds IMDNQ9 ($IC_{50}$=4.07 µM) and IMDNQ5 ($IC_{50}$=2.27 µM) and in compounds IMDNQ8 ($IC_{50}$=2.67 µM) and IMDNQ6 ($IC_{50}$=1.51 µM). When the 3-chloro-group is substituted with a 3-bromo group a slight increase in cytotoxicity on Balb/C 3T3 mouse fibroblast cell line is seen in compounds IMDNQ9 ($IC_{50}$=21.83 µM) versus IMDNQ5 ($IC_{50}$=12.83 µM); and compound IMDNQ8 ($IC_{50}$=26.50 µM) versus IMDNQ6 ($IC_{50}$=14.17 µM).

The ratio between the toxic dose and the therapeutic dose of a drug is a selectively index. It is used as a measure of the relative safety of the drug for a particular treatment. The selectivity index (SI) herein is the ratio of $IC_{50}$ for fibroblast cells/$IC_{50}$ for parasites and was calculated to compare the toxicity for mammalian cells and the activity against *T. cruzi*. The presently prescribed nifurtimox has a selectivity index of 10.86. In vitro testing demonstrates that the present method can be significantly and unexpectedly more selective against *Trypanosoma cruzi*. In one aspect of the method, the selectivity index is at least about 300% greater than the selectivity index for nifurtimox. For example, the IMDNQ1, IMDNQ2, IMDNQ3 and IMDNQ10 compounds exhibited selectivity indices of 60.25, 53.97, 31.83 and 275.3, respectively, in in vitro testing against *Trypanosoma cruzi*. Further, in an aspect of the invention, representative compounds are relatively non-cytotoxic to Balb/C 3T3 mouse fibroblast cell line with $IC_{50}$ values of well over 100 µM.

The in vitro testing shows the present method should have in vivo efficacy in inhibiting proliferation of *Trypanosoma* cruzi, and thus indicating a disease caused by the trypanosome can be treated by administering a compound according to the general formula.

Inhibitory concentration is typically evaluated at the 50% inhibitory concentration ($IC_{50}$). Inhibition of proliferation may be attained at a lower concentration in practice, but an $IC_{50}$ concentration may be desirable.

Representative imido-substituted 1,4-napthoquinone compounds, and their synthesis, are described in Bakare, O., et al, Synthesis and MEK1 inhibitory activities of imido-substituted 2-chloro-1,4-naphthoquinones. *Bioorg. Med. Chem.,* 11, 3165-3170 (2003); Berhe, S., et al., Microwave-assisted synthesis of imido-substituted 2-chloro-1,4-naphthoquinone derivatives and their cytotoxic activities on three human prostate cancer cell lines, *Lett. Drug Des. Discov.,* 5, 485-488 (2008); Akinboye et al., Acta Cryst. E65, o24 (2009), and Akinboye et al., Acta Cryst. E65, o277 (2009), the complete disclosures of which are incorporated herein by reference.

A patient in need of treatment may be diagnosed by testing and by physical examination. Testing includes serological tests, immunoassays and PCR methods to diagnose for the presence of *Trypanosoma cruzi* infection in an individual. The testing is sometimes performed in tandem. Serological testing of blood samples from an individual can yield negative and positive sero results. A so-called sero-positive result is indicative of infection. So-called sero-negative results may or may not indicate the absence of infection. Sero-negative results may be useful in assessing possible cure after an individual has completed treatment for *Trypanosoma cruzi*. However, due to the disease progression more than a single test with a single sero-negative result is preferred. PCR methods can be used in determining a patient in need of treatment, and such methods include those described in Galvão et al., PCR Assay for Monitoring *Trypanosoma cruzi* Parasitemia in Childhood after Specific Chemotherapy, J. Clin. Microbiology, 5066-70 (November 2003); Gomes et al., Chagas disease diagnosis: comparative analysis of parasitologic, molecular and serological methods, Am. J. Trp. Med. Hyg. 60:205-210 (1999). Since *Trypanosoma cruzi* releases antigenic material, including tubulin, in an infected mammalian host, monitoring for the presence of tubulin in urine may assist in early diagnosis of Chagas disease. Microscopic examination of fresh anticoagulated blood samples may also be useful. A combination of tests can be useful in monitoring the progress of treatment.

Diagnosis of a patient in the acute phase of Chagas disease who is in need of treatment may include physical examination. The acute stage may extend for a few weeks or months following initial infection. Many symptoms may not be unique to Chagas disease. However, a commonly recognized marker of the acute stage is Romaña's sign, which includes swelling of eyelids on the side of the patient's face nearest the bite or where feces from the vector were deposited or rubbed into the eye.

The methods described herein advantageously utilize an active ingredient selected from 3-imido-substituted 1,4-naphthoquinones, such as 3-imido-substituted 2-alkoxy 1,4-napthoquinones and 3-imido-substituted 2-halo-1,4-naphthoquinones, as a novel class of selective antitrypanosomal agents effective against *Trypanosoma cruzi*.

The expression imido-substituted 1,4-naphthoquinone includes a compound according to the general formula.

Those skilled in the art will recognize that modifications and variations may be made without departing from the true spirit and scope of the invention. The invention, therefore, is not to be limited to the embodiments described and illustrated in the following non-limiting examples but is to be determined from the appended claims.

EXAMPLES

In the Examples, reactions were carried out using laboratory grade materials and solvents. Melting points were determined in open capillary tubes on a Mel-Temp melting point apparatus and are uncorrected. The IR spectra were recorded on a Perkin Elmer PE 100 spectrometer with an Attenuated Total Reflectance (ATR) window. The $^1$H- and $^{13}$C-NMR spectra were obtained on a Bruker Avance 400 MHz spectrometer in deuterated chloroform ($CDCl_3$). Chemical shifts are in δ units (ppm) with TMS (0.00 ppm) or $CHCl_3$ (7.26 ppm), as internal standard for $^1$H-NMR, and $CDCl_3$ (77.00 ppm) for $^{13}$C-NMR. Electrospray ionization mass spectrometry was recorded on a Thermo LTQ Orbitrap XL mass spectrometer and compounds dissolved in acetonitrile with 0.1% formic acid. The known intermediates were prepared according to procedures that are reported in the literature. 2-Amino-3-bromo-1,4-naphthoquinone was prepared by refluxing commercially available 2,3-dibromo-1,4-naphthoquinone with ammonia/ammonium hydroxide mixture in ethanol.

Examples 1-3

The succinimidyl (IMDNQ1), phthalimidyl (IMDNQ2) and dibutytryl (IMDNQ3) derivatives were synthesized from 2-amino-3-chloro-1,4-naphthoquinone and the appropriate acid chloride in accordance with Bakare, O., et al, Synthesis and MEK1 inhibitory activities of imido-substituted 2-chloro-1,4-naphthoquinones. *Bioorg. Med. Chem.,* 11, 3165-3170 (2003); and Berhe, S., et al., Microwave-assisted synthesis of imido-substituted 2-chloro-1,4-naphthoquinone derivatives and their cytotoxic activities on three human prostate cancer cell lines, *Lett. Drug Des. Discov.,* 5, 485-488 (2008).

Example 4

The morpholine dione analog (IMDNQ4) was synthesized by microwave irradiation of a mixture of 2-amino-3-chloro-1,4-naphthoquinone and diglycolyl chloride as depicted in scheme 1 in Berhe, S., et al., Microwave-assisted synthesis of imido-substituted 2-chloro-1,4-naphthoquinone derivatives and their cytotoxic activities on three human prostate cancer cell lines, *Lett. Drug Des. Discov.,* 5, 485-488 (2008).

Examples 5-10

A general procedure for the synthesis of arylimido-substituted 1,4-naphthoquinones represented by the formula

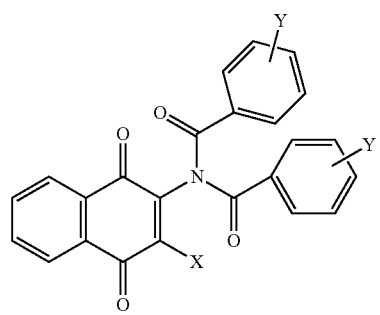

wherein X is halogen and Y is halogen is exemplified with respect to IMDNQ5-IMDNQ10, respectively in Examples 5 through 10. 2-Amino-3-chloro-1,4-naphthoquinone (1.47 mmol) or the 3-bromo-analog was dissolved in THF (15 mL). NaH (3.08 mmol) was added and the mixture stirred at room temperature for 15 min. Appropriate acid chloride (3.08 mmol) was added drop wise, and the resulting mixture stirred at room temperature for 24 hours. The THF was then evaporated under vacuum and ice-cooled water added to the residual mixture. The resulting aqueous mixture was extracted with $CH_2Cl_2$ (2×30 mL) and the combined organic phase washed with water (3×15 mL), saturated NaCl solution (15 mL) and dried over anhydrous $MgSO_4$. The crude product was purified by triturating in hot ethanol followed by recrystallization in ethyl acetate and/or column chromatography on silica gel.

N-(3-Bromo-1,4-dioxo-1,4-dihydronaphthalen-2-yl)-4-fluoro-N-(4-fluorobenzoyl)-benzamide (IMDNQ 5): Yellow solid (66%). Mp: 170-172° C. IR (cm$^{-1}$) 1719.23, 1670.56, 1596.69, 1505.57. $^1$H NMR (CDCl$_3$) 7.05 (t, 4H, J=12.0 Hz), 7.77-7.88 (m, 6H), 8.08-8.15 (m, 1H), 8.21-8.27 (m, 1H). $^{13}$C NMR (CDCl$_3$) 115.57, 115.79, 127.4, 127.71, 130.18, 130.30, 130.33, 130.85, 131.35, 131.44, 134.46, 134.50, 138.52, 146.90, 165.03, 169.91, 176.96, 177.97. ESI MS m/z 517.9785 ([M+Na]$^+$ calcd 517.9815).

N-(3-Bromo-1,4-dioxo-1,4-dihydronaphthalen-2-yl)-2-chloro-N-(2-chlorobenzoyl)-benzamide (IMDNQ 6): Yellow crystal (34%). Mp 232-234° C. IR (cm$^{-1}$) 1728.78, 1688.76, 1671.10, 1588.22, 1468.70. $^1$H NMR (CDCl$_3$) 7.13 (☐☐d, 2H, J=7.9 Hz), 7.21 (☐☐dd, 2H, J=1.6, 7.9 Hz), 7.28 (dd, 2H, J=1.3, 7.5 Hz), 7.78-7.86 (m, 2H), 7.94 (d, 2H, 5.2 Hz), 8.15-8.21 (m, 1H), 8.22-8.28 (m, 2H). $^{13}$C NMR (CDCl$_3$) 126.65, 127.66, 128.08, 129.63, 130.49, 130.81, 131.23, 132.25, 134.68, 134.80, 140.78, 145.81, 167.57, 177.26, 177.81. ESI MS m/z 549.9240 ([M+Na]$^+$ calcd 549.9224).

4-Chloro-N-(4-chlorobenzoyl)-N-(3-chloro-1,4-dioxo-1,4-dihydronaphthalen-2-yl)-benzamide (IMDNQ 7): Yellow solid. (27%). Mp 212-213° C. IR (cm$^{-1}$) 1737.38, 1714.75, 1696.91, 1673.62, 1589.20, 1571.10. $^1$H NMR (CDCl$_3$) 7.33-7.36 (m, 4H), 7.68-7.72 (m, 4H), 7.79-7.85 (m, 2H), 8.09-8.11 (m, 1H), 8.20-8.22 (m, 1H). $^{13}$C NMR (CDCl$_3$) 127.72, 127.80, 129.18, 130.34, 130.50, 131.32, 132.52, 134.92, 134.95, 139.67, 142.46, 143.87, 170.40, 177.05, 178.59. ESI MS m/z 505.975 ([M+Na]$^+$ calcd 505.973).

2-Chloro-N-(2-chlorobenzoyl)-N-(3-chloro-1,4-dioxo-1,4-dihydronaphthalen-2-yl)-benzamide (IMDNQ 8): Yellow solid. (49%). Mp 217-218° C. IR (cm$^{-1}$) 1720.19, 1681.22, 1618.00, 1588.02. $^1$H NMR (CDCl$_3$) 7.10-7.16 (m, 2H), 7.21-7.31 (m, 4H), 7.79-7.89 (m, 4H), 8.17-8.20 (m, 1H), 8.20-8.26 (m, 1H). $^{13}$C NMR (CDCl$_3$) 126.76, 126.93, 127.60, 127.80, 129.69, 130.54, 130.85, 131.37, 132.36, 132.52, 132.56, 132.75, 134.14, 134.75, 134.91, 142.65, 144.43, 177.13, 178.22. ESI MS m/z 505.9741 ([M+Na]$^+$ calcd 505.9730).

N-(3-Chloro-1,4-dioxo-1,4-dihydronaphthalen-2-yl)-4-fluoro-N-(4-fluorobenzoyl)-benzamide (IMDNQ 9): Yellow solid. (56%). Mp 284-286° C. IR (cm$^{-1}$) 3074.94, 1719.61, 1689.97, 1672.75, 1591.10. $^1$H NMR (CDCl$_3$) 7.00-7.06 (m, 1H), 7.75-7.85 (m, 1H), 8.10-8.12 (m, 6H), 8.20-8.22 (m, 4H). $^{13}$C NMR (CDCl$_3$) 115.97, 116.19, 116.41, 126.65, 126.96, 127.67, 127.77, 130.53, 130.57, 130.58, 131.35, 131.62, 131.71, 132.75, 134.88, 142.42, 144.13, 164.14, 166.68, 170.33, 177.13, 178.63. ESI MS m/z 474.034 ([M+Na]$^+$ calcd 474.032).

3-Chloro-N-(3-chlorobenzoyl)-N-(3-chloro-1,4-dioxo-1,4-dihydronaphthalen-2-yl)-benzamide (IMDNQ 10): Yellow solid. (31%). Mp 258-260° C. IR (cm$^{-1}$) 3075.36, 1713.64, 1698.11, 1672.50, 1591.48, 1571.31. $^1$H NMR (CDCl$_3$) 7.27-7.31 (t, J=7.85 Hz, 2H), 7.42-7.45 (ddd, J=1.03, 2.09, 8.07 Hz, 2H), 7.60-7.63 (td, J=1.07, 7.68 Hz, 2H), 7.70-7.71 (t, J=1.82, 2H), 7.80-7.85 (m, 2H), 8.11-8.14 (m, 1H), 8.21-8.23 (m, 1H). $^{13}$C NMR (CDCl$_3$) 127.02, 127.93, 128.03, 129.34, 130.21, 130.75, 131.55, 133.29, 135.14, 135.21, 136.06, 143.00, 143.84, 170.20, 177.25, 178.66. ESI MS m/z 505.9741 ([M+Na]$^+$ calcd 505.9730).

Example 11

The bis-(chloroacetyl)-derivative (IMDNQ11) was prepared by heating 2-amino-3-chloro-1,4-naphthoquinone in excess 2-chloroacetyl chloride at high temperatures as shown in scheme 1 in Bakare, O., et al, Synthesis and MEK1 inhibitory activities of imido-substituted 2-chloro-1,4-naphthoquinones. *Bioorg. Med. Chem.*, 11, 3165-3170 (2003) (2003); and Berhe, S., et al., Microwave-assisted synthesis of imido-substituted 2-chloro-1,4-naphthoquinone derivatives and their cytotoxic activities on three human prostate cancer cell lines, *Lett. Drug Des. Discov.*, 5, 485-488 (2008).

Example 12

Synthesis of 2,3-dimethoxy-1,4-naphthoquinone is shown below:

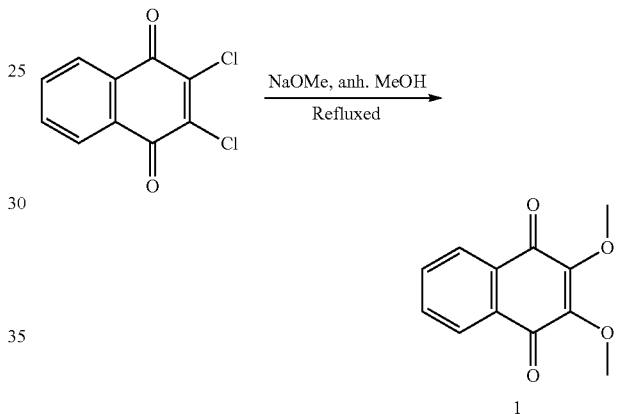

A mixture of 2,3-dichloro1,4-naphthoquinone (4.960 g, 0.022 mol) and NaOMe (3.582 g, 0.066 mol) was refluxed at 80° C. for 5 hrs in anhydrous MeOH (100 mL). A second amount of NaOMe (2.365 g, 0.044 mol) was added and the mixture was refluxed for 1 hr. The reaction mixture was concentrated, filtered and the residue was repeatedly washed with ice-cold water to obtain a yellow solid. (3.463 g, 72.7%).

For a different alkoxy or aryloxy substitution on the 2,3 positions of the 1,4-naphthoquinone, an appropriate alkali alkoxide can be selected. In turn, this will lead to X being a different alkoxy or aryloxy subtitutent than reported in Examples 13-19.

Example 13

Synthesis of 2-amino-3-methoxy-1,4-naphthoquinone is shown below:

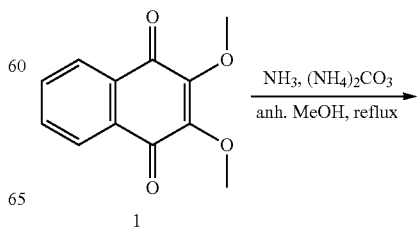

-continued

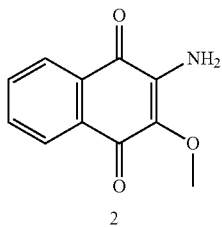
2

NH₃ was continuously bubbled through a mixture of 1 (305 mg, 1.40 mmol) and (NH₄)₂CO₃ (439 mg, 4.57 mmol) in anhydrous MeOH (70 mL). The reaction mixture was refluxed at 50° C. for 2 hrs. Another (NH₄)₂CO₃ (418 mg, 4.35 mmol) was added to the cooled solution and the mixture was again refluxed for 1 hr. Argon was bubbled through the cooled solution for 10 mins. The solution was evaporated to dryness in vacuo, ice-cold water (20 mL) was added and precipitate was filtered to obtain a red solid. (226 mg).

Examples 14 to 19

Synthesis of 2-imido-3-methoxy 1,4-napthoquniones (3)-(8), respectively Examples 14 to 19, is shown below:

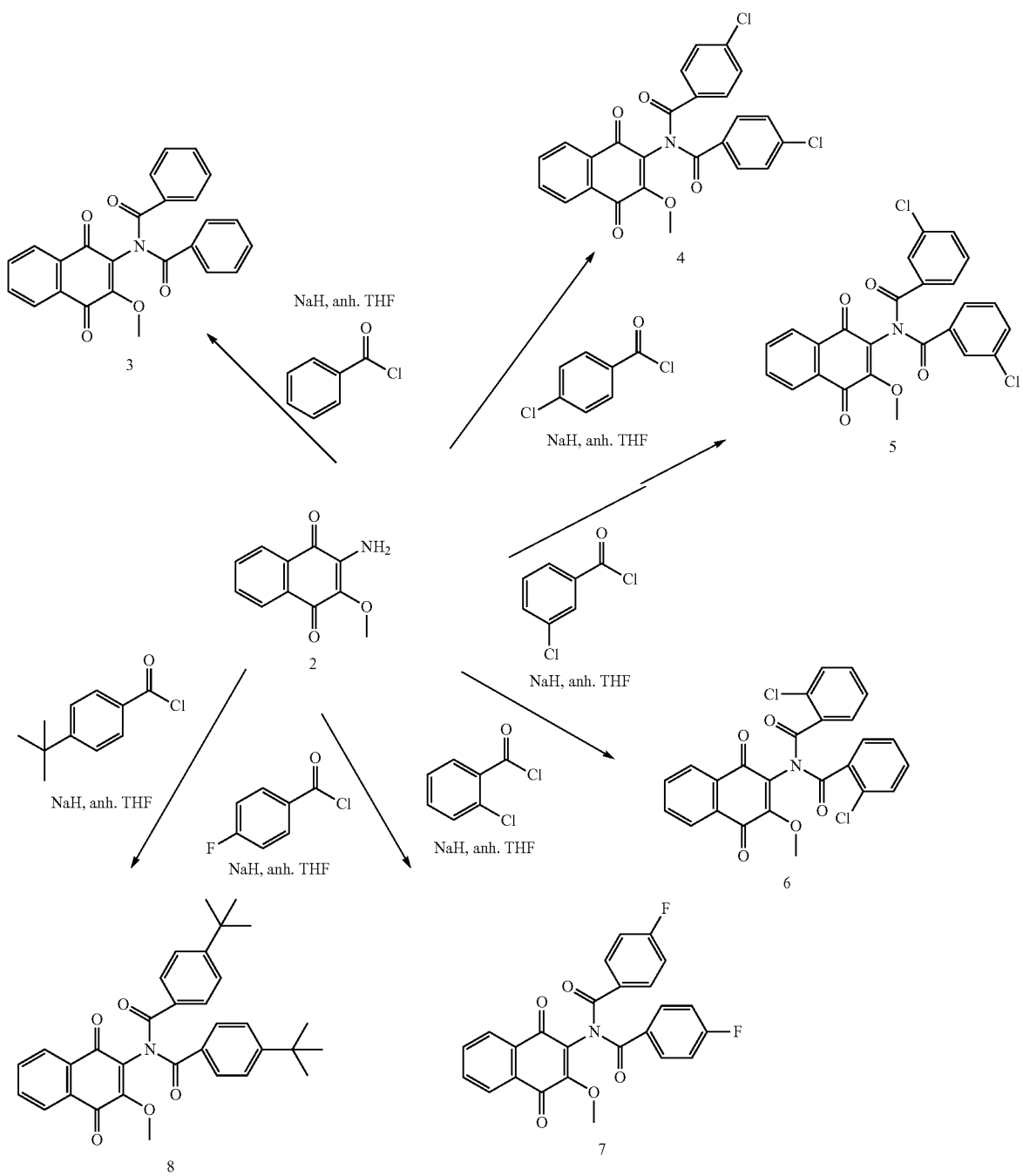

A solution of 2,3-dimethoxy-1,4-naphthoquinone (200 mg, 0.984 mmol) in anhydrous THF (20 mL) was stirred at room temperature. NaH (54 mg, 2.26 mmol) was added and the resulting mixture was stirred at room temperature for 30 mins. The respective acid chlorides (2.3 mole ratio) were added and the reaction was stirred at room temperature for 24 hrs. The reaction mixture was concentrated under vacuum and ice-water mixture (20 mL) was added. The aqueous layer was extracted with dichloromethane (4×10 mL) and the combined organic layer washed with water (3×15 mL), saturated sodium chloride solution and dried over anhydrous $MgSO_4$. The solvent was removed in vacuo and the residue triturated in ethanol (2 mL) and filtered. Further purification was done by recrystallization in EtOH or EtOAc and column chromatography on silica gel with 100% DCM.

Variants of compound 8 are possible, and instead of a t-butyl substituent, other reactants represented the formula:

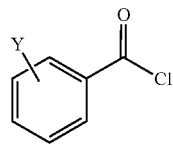

can be used wherein Y represents a substituent other than t-butyl. For example, the substituent Y can be alkyl. The alkyl can be lower alkyl. Exemplary alkyls include $C_1$-$C_5$ alkyl, such as methyl, ethyl, propyl, iso-propyl, butyl, iso-butyl, pentyl, iso-amyl, as examples.

Examples 20 to 26

2-amino-3-chloro-1,4-naphthoquinone or 2-amino-3-bromo-1,4-naphthoquinone was dissolved in THF (15 mL). NaH was added and the mixture was stirred at room temperature for 15 mins. The appropriate acid chloride was added, drop wise, and the mixture was stirred for 24 hours. (Mole ratio of Substrate:NaH:Acid Chloride (1:2.3:2.3)) THF was evaporated under vacuum and the mixture was washed with ice-water (10 g ice and 10 mL water). The ice-water mixture was extracted with $CH_2Cl_2$ (30 mL, 20 mL consecutively) and the combined organic phase washed with water (3×20 mL), saturated NaCl solution (3×20 mL), then dried over anhydrous $MgSO_4$. The crude was purified via triturating in hot ethanol, recrystallization in ethyl acetate and/or via column chromatography.

2-Dibenzoylamino-3-chloro-1,4-naphthoquinone

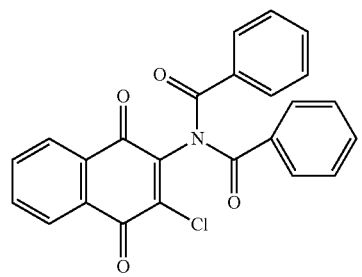 [SMILES: O=C1C(Cl)=C(N(C(=O)c2ccccc2)C(=O)c2ccccc2)C(=O)c2ccccc21]

Obtained a yellow solid. (61.3%). Mp 294-297° C. IR ($cm^{-1}$) 3328.00, 1698.21, 1672.91, 1618.25, 1590.78, 1573.45. $^1$H NMR (DMSO-$d_6$) 7.35-7.39 (t, J=7.5 Hz, 4H), 7.46-7.50 (tt, J=1.2, 7.5 Hz, 2H), 7.65-7.67 (m, 4H), 7.83-7.90 (m, 2H), 7.94-7.96 (dd, J=1.7, 7.4 Hz, 1H), 8.04-8.06 (dd, J=1.3, 8.2 Hz, 1H). $^{13}$C NMR ($CDCl_3$) 127.61, 127.64, 128.59, 129.11, 130.69, 131.37, 132.90, 134.45, 134.68, 134.73, 142.32, 144.33, 171.59, 177.29, 178.59.

2-Dibenzoylamino-3-bromo-1,4-naphthoquinone

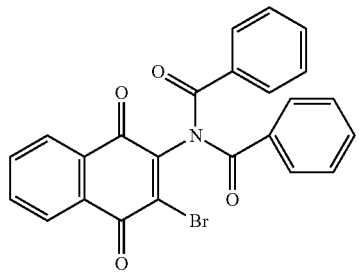

Obtained a yellow solid. (53.1%). Mp 234-238° C. IR ($cm^{-1}$) 3087.51, 1693.21, 1671.24, 1588.29, 1570.41. $^1$H NMR ($CDCl_3$) 7.30-7.34 (t, J=7.40 Hz, 4H), 7.41-7.45 (tt, J=1.21, 7.49 Hz, 2H), 7.77-7.81 (m, 6H), 8.10-8.12 (m, 1H), 8.20-8.22 (m, 1H). $^{13}$C NMR ($CDCl_3$) 127.72, 127.96, 128.58, 129.22, 130.65, 131.22, 132.89, 134.58, 134.68, 134.70, 138.75, 147.47, 171.55, 177.48, 178.30.

2-bis-(3-chlorobenzoyl)amino-3-bromo-1,4-naphthoquinone

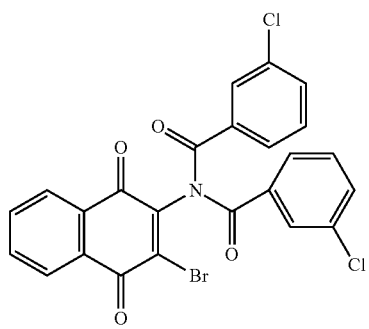 [SMILES: O=C1C(Br)=C(N(C(=O)c2cccc(Cl)c2)C(=O)c2cccc(Cl)c2)C(=O)c2ccccc21]

Obtained a yellow solid (25.9%) Mp 204-206° C. IR ($cm^{-1}$) 3074.53, 1698.10, 1671.33, 1589.07, 1566.99. $^1$H NMR ($CDCl_3$) 7.28 (t, 2H, J=7.90), 7.38-7.46 (m, 2H), 7.60-7.66 (m, 2H), 770-7.5 (t, 2H, J=1.8 Hz), 7.78-7.85 (m, 2H), 8.09-8.15 (m, 1H), 8.19-8.26 (m, 2H). $^{13}$C NMR ($CDCl_3$) 127, 128.09, 128.40, 129.49, 130.25, 130.78, 131.49, 133.32, 135.15, 135.18, 135.24, 136.25, 139.56, 147.05, 170.21, 177.50, 178.43.

2-bis-(4-chlorobenzoyl)amino-3-bromo-1,4-naphthoquinone

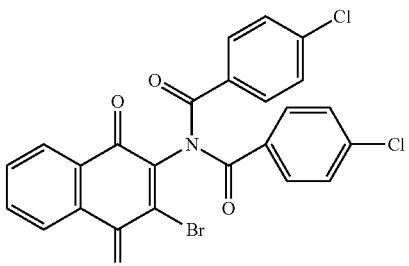

Obtain a yellow solid. (34.3%). Mp 266-269° C. IR (cm$^{-1}$) 3096.94, 1703.69, 1661.23, 1586.85. $^1$H NMR (CDCl$_3$) 7.33-7.36 (dd, J=2.16, 8.47 Hz, 4H), 7.70-7.73 (dd, J=2.37, 8.53 Hz, 4H), 7.79-7.82 (m, 2H), 8.08-8.11 (m, 1H), 8.20-8.22 (m, 1H). $^{13}$C NMR (CDCl$_3$) 127.80, 128.09, 129.13, 130.41, 130.46, 131.17, 132.66, 134.84, 134.90, 138.94, 139.61, 146.98, 170.32, 177.21, 178.28.

2-bis-(4-tert-butylbenzoyl)amino-3-chloro-1,4-naphthoquinone

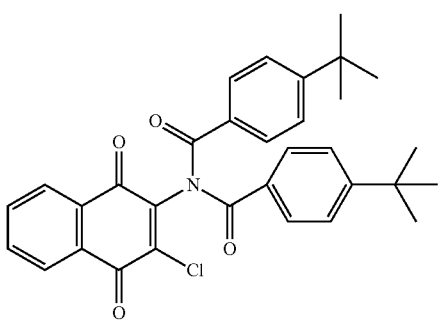 [SMILES: CC(C)(C)c1ccc(C(=O)N(C(=O)c2ccc(C(C)(C)C)cc2)C2=C(Cl)C(=O)c3ccccc3C2=O)cc1]

Obtain yellow solid. (27.9%). Mp 257-260° C. IR (cm$^{-1}$) 2965.11, 2901.26, 2868.04, 1701.21, 1673.45, 1603.90, 1592.73, 1572.41. $^1$H NMR (CDCl$_3$) 8.22-8.18 (m, 1H), 8.13-809 (m, 1H), 7.81-7.78 (m, 2H), 7.69-7.67 (dd, 4H, J=8.57, 1.86 Hz), 7.32-7.30 (dd, 4H, J=8.53, 1.81 Hz), 1.25 (s, 18H). $^{13}$C NMR (CDCl$_3$) 30.96, 35.06, 125.51, 127.60, 127.65, 129.14, 130.82, 131.45, 131.71, 134.62, 134.68, 142.09, 144.58, 156.57, 171.66, 177.51, 178.67.

2-bis-(4-methoxybenzoyl)amino-3-chloro-1,4-naphthoquinone

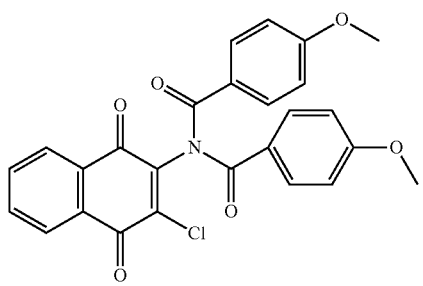 [SMILES: COc1ccc(C(=O)N(C(=O)c2ccc(OC)cc2)C2=C(Cl)C(=O)c3ccccc3C2=O)cc1]

Obtain a yellow solid. (47.9%). Mp 283-287° C. IR (cm$^{-1}$) 3019.56, 1698.7, 1668.81, 1599.28, 1574.26, 1508.65. $^1$H NMR (CDCl$_3$) 3.81 (s, 6H), 6.80-6.84 (td, J=2.86, 8.95 Hz, 4H), 7.73-7.82 (m, 6H), 8.09-8.11 (m, 1H), 8.19-8.21 (m, 1H). $^{13}$C NMR (CDCl$_3$) 55.48, 113.98, 114.21, 126.76, 127.57, 127.64, 130.38, 130.79, 131.41, 131.48, 134.61, 134.66, 141.69, 144.95, 163.34, 171.03, 177.48, 178.77.

2-bis-(3,4,5-trimethoxybenzoyl)amino-3-chloro-1,4-naphthoquinone

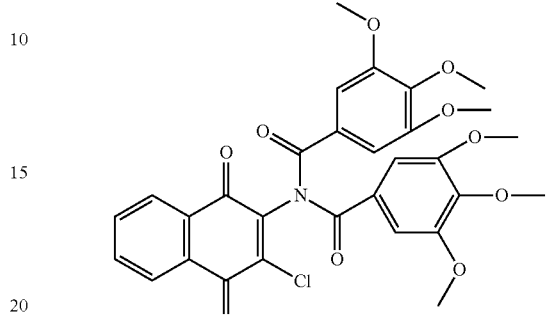

Obtain orange crystals (51.6%). Mp 171-172° C. IR (cm$^{-1}$) 3015.37, 2939.81, 2838.40, 1704.21, 1675.26, 1586.02, 1122.75. $^1$H NMR (CDCl$_3$) 3.81 (s, 12H), 3.84 (s, 6H), 7.02 (s, 4H), 7.81-7.84 (m, 2H), 8.12-8.14 (m, 1H), 8.22-8.24 (m, 1H). $^{13}$C NMR (CDCl$_3$) 56.27, 56.35, 60.93, 127.62, 127.77, 129.31, 130.69, 131.39, 134.86, 142.06, 142.27, 144.45, 153.01, 171.08, 177.27, 178.84.

Example 27

An unsymmetrical analog was also synthesized either by first forming the amide derivative via heating 2-amino-3-chloro-1,4-naphthoquinone in p-chlorobenzoyl chloride, or reacting 2-amino-3-chloro-1,4-naphthoquinone, sodium hydride and p-chlorobenzoyl chloride for 5 min at room temperature. Subsequent reaction of the isolated pure amide with NaH followed by addition of benzoyl chloride furnished the unsymmetrical analog in 43% yield.

A syntheses is described for 2-(N-Benzoyl-N-(4-chlorobenzoyl))-amino-3-chloro-1,4-naphthoquinone:

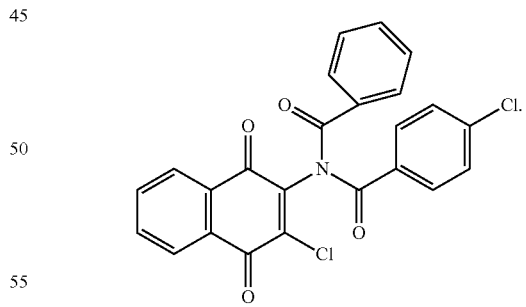

2-Amino-3-chloro-1,4-naphthoquinone (302 mg, 1.45 mmol) was dissolved in THF (15 mL). NaH (104 mg, 4.33 mmol) was added to the solution and the mixture was stirred at room temperature for 30 mins. p-Chlorobenzoyl chloride (0.27 mL, 375 mg, 2.14 mmol) was added and the mixture was stirred for 5 mins. THF was removed under vacuum and the mixture was washed with ice-water (10 g ice and 10 mL water). The ice-water mixture was washed with CH$_2$Cl$_2$ (30 mL) and the organic layer was washed with water (3×15 mL) and saturated NaCl (3×15 mL) then dried over Na$_2$SO$_4$. The crude was recrystallized in 100% EtOH (20 mL) then triturated in 100% ethyl acetate to obtain the 2(p-chlorobenzylamido)-3-chloro-1,4-naphthoquinone. The 2-(p-chlorobenzylamido)-1,4-naphthoquinone (101 mg, 0.292 mmol) was dissolved in THF (15 mL). NaH (14 mg, 0.583 mmol) was added followed by the addition of benzoyl chloride (84.84 mg, 0.604 mmol). The resulting mixture was stirred at room temperature for 26 hours. THF was removed under vacuum and the mixture was washed with ice-water (10 g ice and 10 mL water). The ice-water mixture was washed with $CH_2Cl_2$ (30 mL) and the organic layer was washed with water (3×15 mL) and saturated NaCl (3×15 mL) then dried over $Na_2SO_4$. The crude was purified by column chromatography with silica gel in 100% $CH_2Cl_2$ to obtain a yellow solid. (57 mg, 43.2%). Mp 200-210° C. IR (cm$^{-1}$) 3093.23, 1705.87, 1693.46, 1673.22, 1587.07, 1571.70, 1521.92. $^1$H NMR (CDCl$_3$) 7.30-7.33 (td, J=1.89, 6.72 Hz, 2H), 7.33-7.37 (t, J=7.98 Hz, 2H), 7.45-7.47 (tt, 7.46 Hz, 1H), 7.69-7.72 (td, J=1.96, 8.60 Hz, 2H), 7.73-7.76 (td, J=1.41, 8.49 Hz, 2H), 7.79-7.82 (m, 1H), 8.10-8.13 (m, 1H), 8.20-8.22 (m, 1H). $^{13}$C NMR (CDCl$_3$) 127.68, 127.73, 128.76, 129.00, 129.06, 130.63, 131.37, 133.21, 134.82, 124.84, 171.34, 177.19, 178.60.

Other unsymmetrical imides such as depicted in the structure below can be obtained in similar manner. In these compounds the aryl groups on the imido moiety are different ("unsymmetrical" or "mixed") as follows:

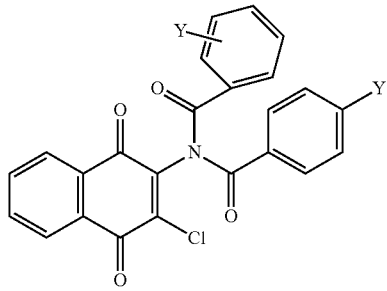

wherein each Y, independent of the other, can be halogen, alkyl, alkoxy, trifluoromethyl. Although the structure illustrated includes one Y in the para position, it should be understood that each Y can be the same or different, and in the same or different positions on their respective aryl rings. Positions in this context means ortho-, meta- or para-positions on each aryl aryl ring in the imido moiety. Thus, each Y can be the same and in the same positions; each Y can be the same but in different positions; each Y can be different but in the same positions; or each Y can be different and in different positions.

Still further, in another aspect, each aryl ring can have multiple substituents, e.g., $(Y)_m$ where m is an integer from 0 to 5, and the various Y substituents can differ based on the acid chlorides from the class of benzoyl chlorides used in the synthesis. It will be appreciated that the acid chloride is not restricted to being selected from the class of benzoyl chlorides when an R group is other than aryl or substituted aryl.

In Example 27 and in its accompanying illustrative formulas, X is chloro but it will be appreciated that X is not restricted to chloro.

Example 28

2-amino-3-chloro-1,4-naphthoquinone was dissolved in THF (15 mL). NaH was added and the mixture was stirred at room temperature for 15 mins. The 4-methoxybenzoyl chloride was added, drop wise, and the mixture was stirred for 24 hours. (Mole ratio of Substrate:NaH:Acid Chloride (1:2.3:2.3)) THF was evaporated under vacuum and the mixture was washed with ice-water (10 g ice and 10 mL water). The ice-water mixture was extracted with $CH_2Cl_2$ (30 mL, 20 mL consecutively) and the combined organic phase washed with water (3×20 mL), saturated NaCl solution (3×20 mL), then dried over anhydrous $MgSO_4$. The crude was purified via triturating in hot ethanol, recrystallization in ethyl acetate and/or via column chromatography.

2-bis-(4-methoxybenzoyl)amino-3-chloro-1,4-naphthoquinone

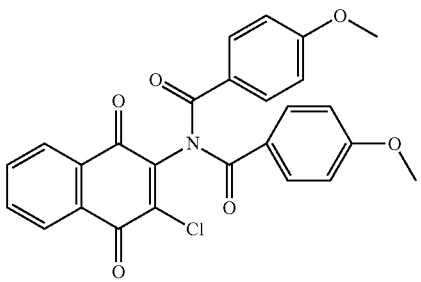 [SMILES: COc1ccc(C(=O)N(C(=O)c2ccc(OC)cc2)C2=C(Cl)C(=O)c3ccccc3C2=O)cc1]

Obtain a yellow solid. (47.9%). Mp 283-287° C. IR (cm$^{-1}$) 3019.56, 1698.7, 1668.81, 1599.28, 1574.26, 1508.65. $^1$H NMR (CDCl$_3$) 3.81 (s, 6H), 6.80-6.84 (td, J=2.86, 8.95 Hz, 4H), 7.73-7.82 (m, 6H), 8.09-8.11 (m, 1H), 8.19-8.21 (m, 1H). $^{13}$C NMR (CDCl$_3$) 55.48, 113.98, 114.21, 126.76, 127.57, 127.64, 130.38, 130.79, 131.41, 131.48, 134.61, 134.66, 141.69, 144.95, 163.34, 171.03, 177.48, 178.77.

Example 29

2-amino-3-chloro-1,4-naphthoquinone was dissolved in THF (15 mL). NaH was added and the mixture was stirred at room temperature for 15 mins. The 3,4,5-(trimethoxy)benzoyl chloride was added, drop wise, and the mixture was stirred for 24 hours. (Mole ratio of Substrate:NaH:Acid Chloride (1:2.3:2.3)) THF was evaporated under vacuum and the mixture was washed with ice-water (10 g ice and 10 mL water). The ice-water mixture was extracted with $CH_2Cl_2$ (30 mL, 20 mL consecutively) and the combined organic phase washed with water (3×20 mL), saturated NaCl solution (3×20 mL), then dried over anhydrous $MgSO_4$. The crude was purified via triturating in hot ethanol, recrystallization in ethyl acetate and/or via column chromatography.

2-bis-(3,4,5-trimethoxybenzoyl)amino-3-chloro-1,4-naphthoquinone

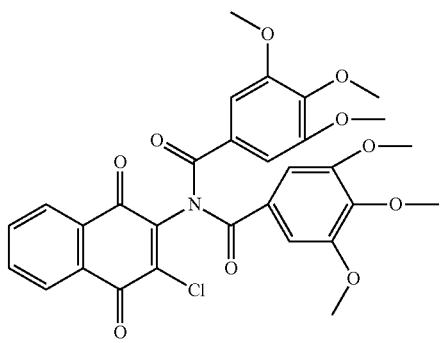 [SMILES: COc1cc(C(=O)N(C(=O)c2cc(OC)c(OC)c(OC)c2)C2=C(Cl)C(=O)c3ccccc3C2=O)cc(OC)c1OC]

Obtain orange crystals (51.6%). Mp 171-172° C. IR (cm$^{-1}$) 3015.37, 2939.81, 2838.40, 1704.21, 1675.26, 1586.02, 1122.75. $^1$H NMR (CDCl$_3$) 3.81 (s, 12H), 3.84 (s, 6H), 7.02 (s, 4H), 7.81-7.84 (m, 2H), 8.12-8.14 (m, 1H), 8.22-8.24 (m, 1H). $^{13}$C NMR (CDCl$_3$) 56.27, 56.35, 60.93, 127.62, 127.77, 129.31, 130.69, 131.39, 134.86, 142.06, 142.27, 144.45, 153.01, 171.08, 177.27, 178.84.

Comparison

Nifurtimox is one of two commercial drugs for Chagas disease and was used as a reference drag.

In Vitro Testing

The antitrypanosomal activity against *Trypanosoma cruzi* was assayed. *Trypanosoma cruzi* epimastigotes (Tulahuen CL98 strain) were cultured in liver infusion trypose (LIT) medium supplemented with 10% fetal bovine serum (FBS) at 28° C., with an inoculum of 1×10$^5$ cells/ml. Different concentrations ranging from 0.39-100 μM of the compounds were added. All assays were carried out in triplicate. Parasites were counted after 48 h using hemocytometers and the concentration that inhibits the parasite's proliferation by 50% (IC$_{50}$) was calculated for each compound.

A cytotoxicity assay was performed with representative analogs IMNDQ1 through IMNDQ11. The cytotoxic effects of the 2-imido-substituted 1,4-naphthoquinones on Balb/C 3T3 mouse fibroblasts (clone A31) were quantitatively assessed using a 3-(4,5-dimethylthiazol-2-yl)-2,5-diphenyltetrazolium bromide (MTT) colorimetric assay. MTT is a yellow tetrazolium salt that is reduced to purple formazan crystals by metabolically active cells. Cells (2.2×10$^4$ cells/well) were seeded in 96-well plate in Improved Minimum Essential Medium (IMEM). Serial dilutions (0.39-100 μM) of the compounds were added. After 48 h incubation at 37° C. in the presence 5% CO$_2$, the medium was aspirated and the cells washed twice to remove traces of chemical compounds. IMEM without phenol containing 10% (v/v) of 3 mg/ml MTT were added to each well. The plates were incubated for 4 h at 37° C. followed by aspiration. The plates were dried for 1 h in a 37° C. incubator. 100 μl of 0.04 N HCl in isopropanol were added to each well and incubated at room temperature (27° C.) in the dark for 2 h to dissolve the formazan crystals. The absorbance was measured spectrophotometrically at 570 nm in a plate reader. The concentration that reduces cell viability by 50% (IC$_{50}$) was calculated for each compound. The toxicity for mammalian cells and the activity against *T. cruzi* were compared by calculating the selectivity index (SI), the ratio of IC$_{50}$ for fibroblast cells/IC$_{50}$ for parasites.

The data were subjected to statistical analysis. All experiments were done in triplicate, the means and standard errors (S.E.) were determined. Data were analyzed by one way ANOVA and Tukey's multiple comparison test using Graph-Pad PRISM software version 5.00. P<0.05 was considered significant.

The antitrypanocidal activity against *Trypanosoma cruzi*, cytotoxicity, and selectivity indices of the eleven imido-substituted 1,4-naphthoquinones and nifurtimox are summarized in Table 1. Each value represents the mean±S.E. of three experiments Testing established 2-imido-substituted 1,4-napthoquinones in Examples 1-11 were more potent antitrypanosomal agents against *T. Cruzi* than nifurtimox. For example, in vitro testing the cyclic and acyclic 2-imido-substituted 3-halo 1,4-naphthoquinone derivatives revealed potent antitrypanosomal properties against *Trypanosoma cruzi* thus demonstrating efficacy in inhibiting proliferation of *Trypanosoma cruzi*.

Certain of the compounds unexpectedly additionally exhibited relatively low cytotoxicity against mammalian cells. Cyclic imido-substituted 1,4-naphthoquinones may have relatively low cytotoxicity. For instance, the IMDNQ1 analog surprisingly was relatively non-cytoxic to the Balb/C 3T3 mouse fibroblast cell line with IC$_{50}$ values of well over 100 μM. The phthalimidyl-substituted 1,4-napthoquinones may have relatively low cytoxicity. For instance, the IMDNQ2 analog surprisingly was relatively non-cytoxic to the Balb/C 3T3 mouse fibroblast cell line with IC$_{50}$ values of well over 100 μM. Meta-halogenated aryl imido-substituted 1,4-naphthoquinones may have relatively low cytotoxicity. For instance, the IMDNQ10 analog surprisingly was relatively non-cytoxic to the Balb/C 3T3 mouse fibroblast cell line with IC$_{50}$ values of well over 100 μM.

Figure 5:
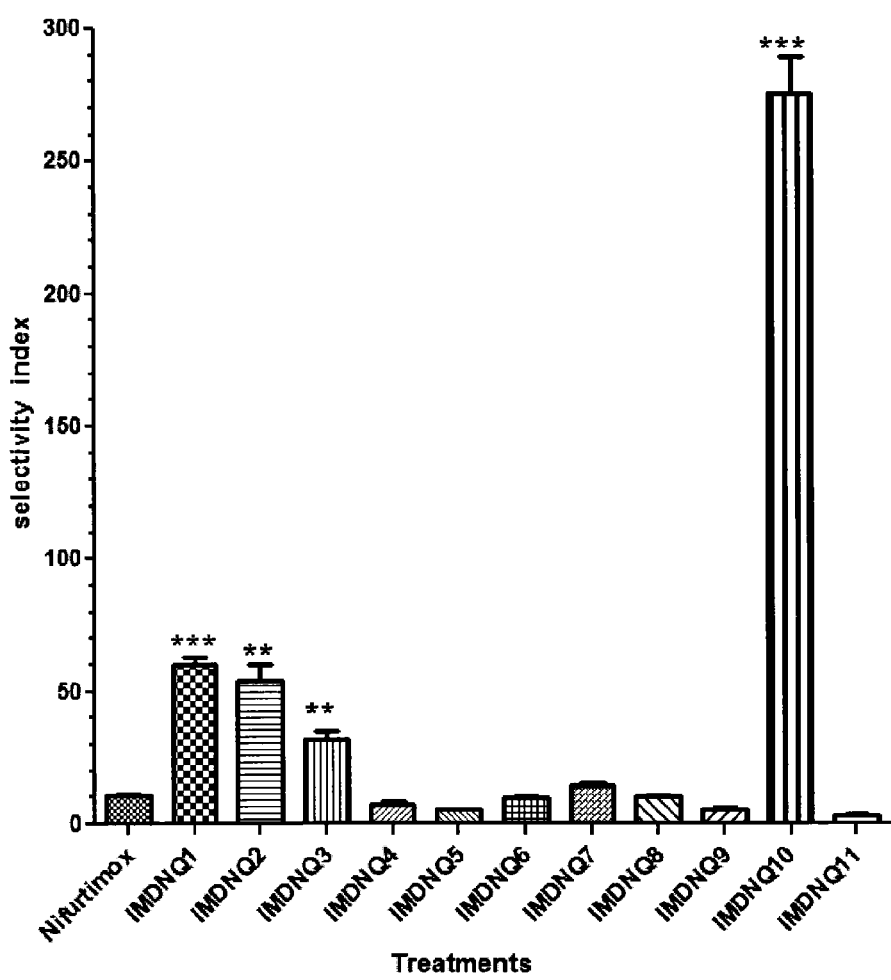
FIG. 5 is a bar graph showing the selectivity indices of certain imido-substituted 1,4-naphthoquinones. Results were expressed as means±S.E. of three experiments. $P<0.01$, *$P<0.0001$ compared with Nifurtimox.
Figure 6C:
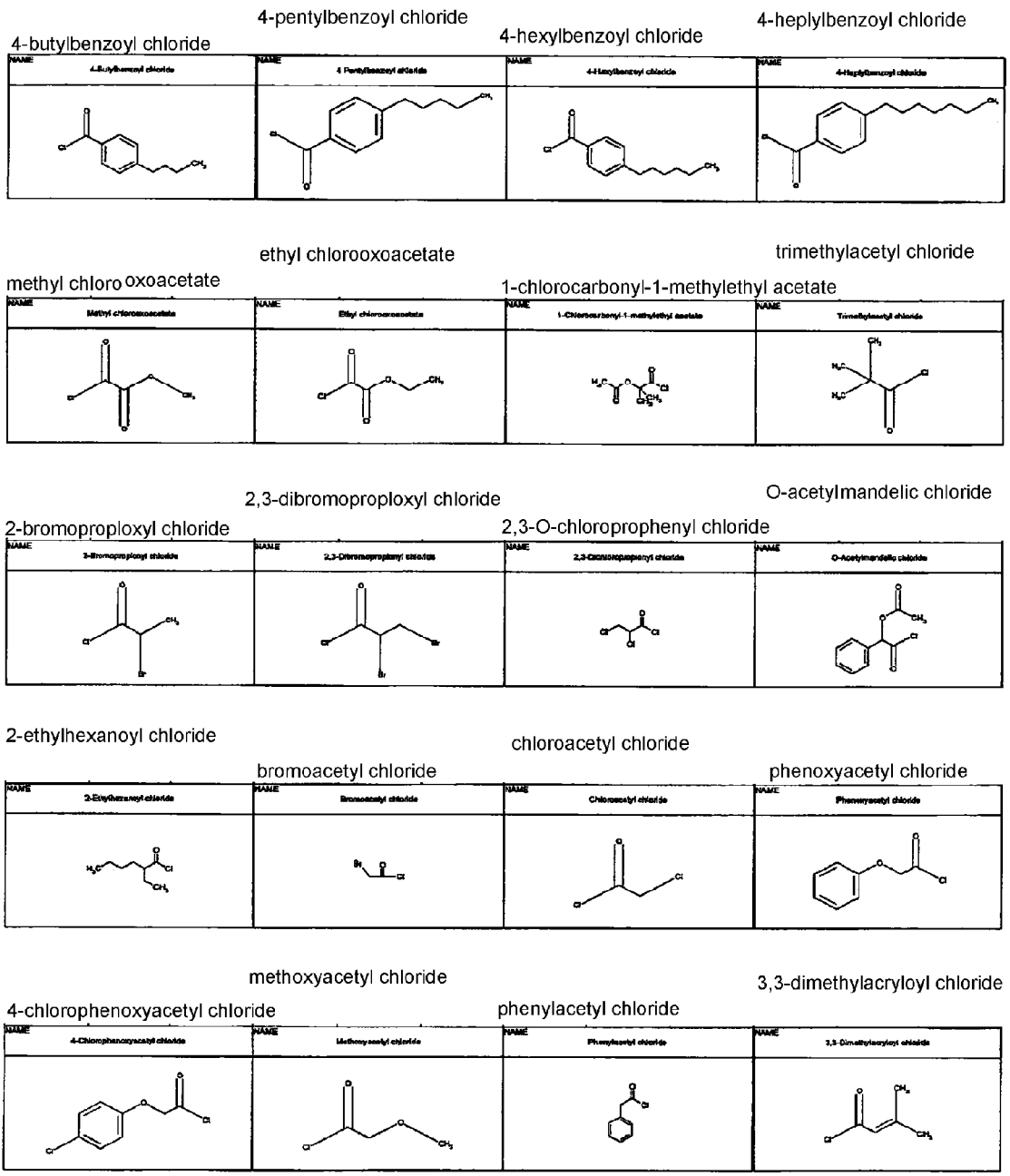
FIGS. 6A through 6X show structures of exemplary acid halide compounds useful in preparing imido-substituted 1,4-naphthoquinones.
Figure 6D:
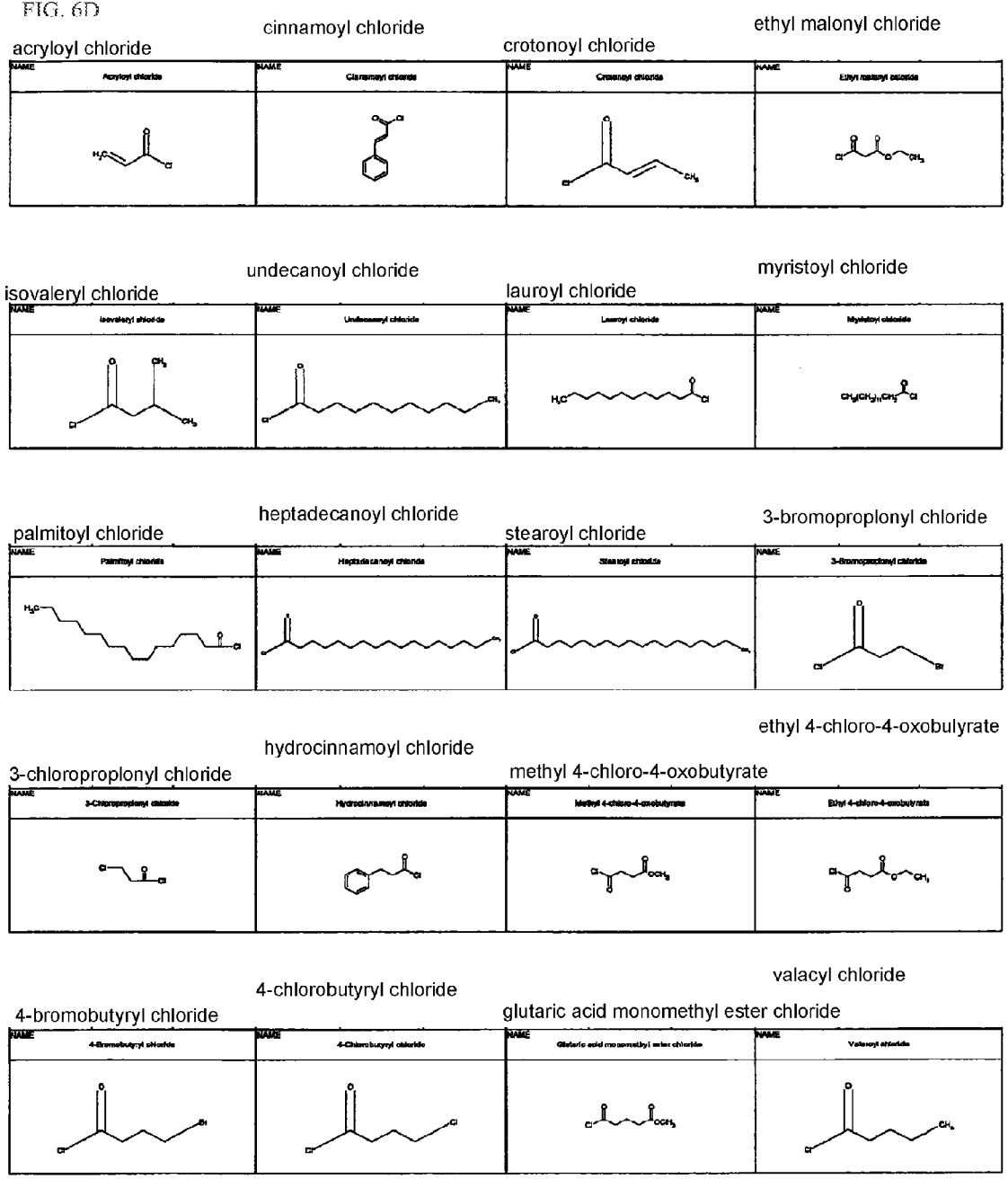
Figure 6E:
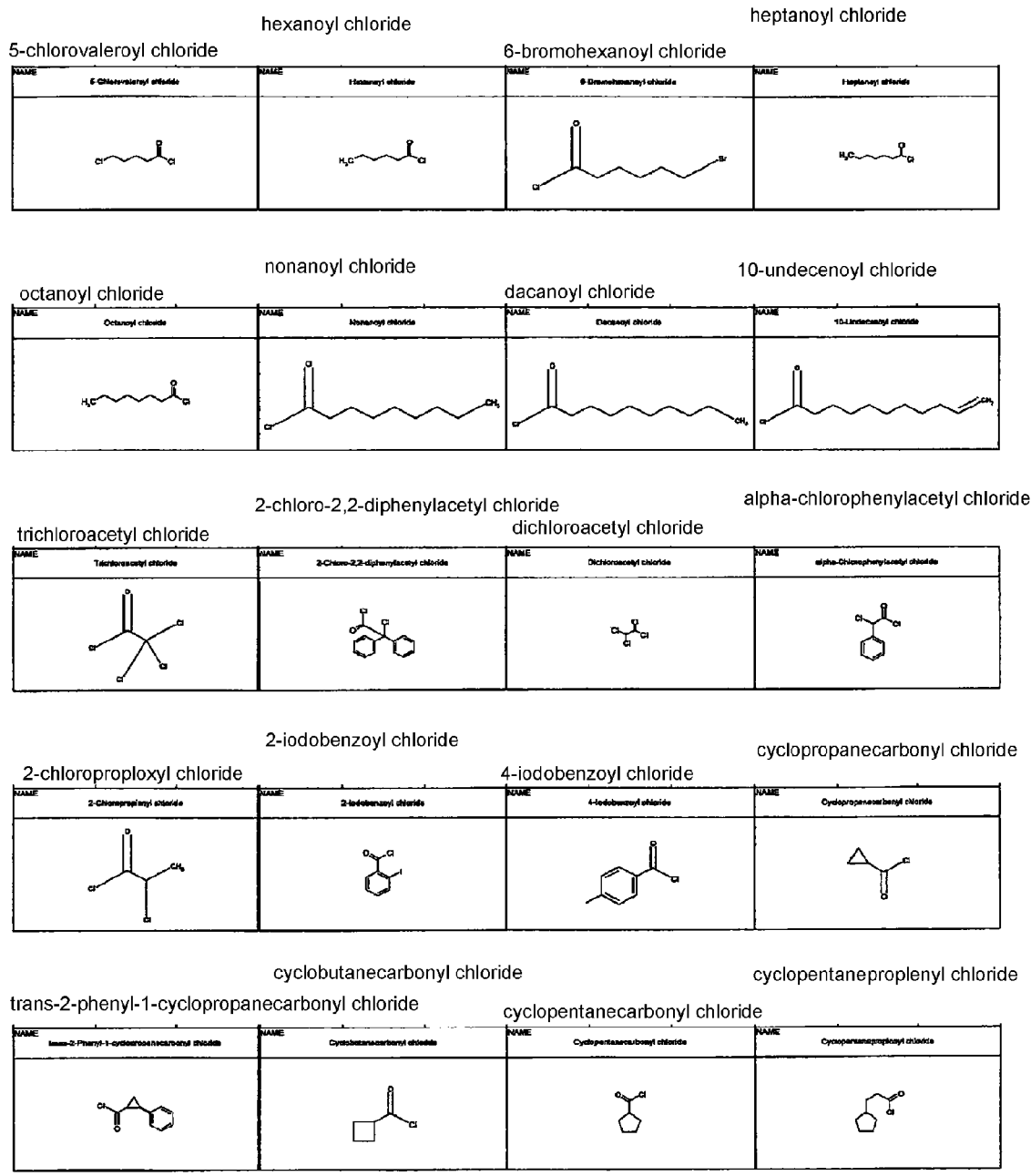
Figure 6G:
Figure 6I:
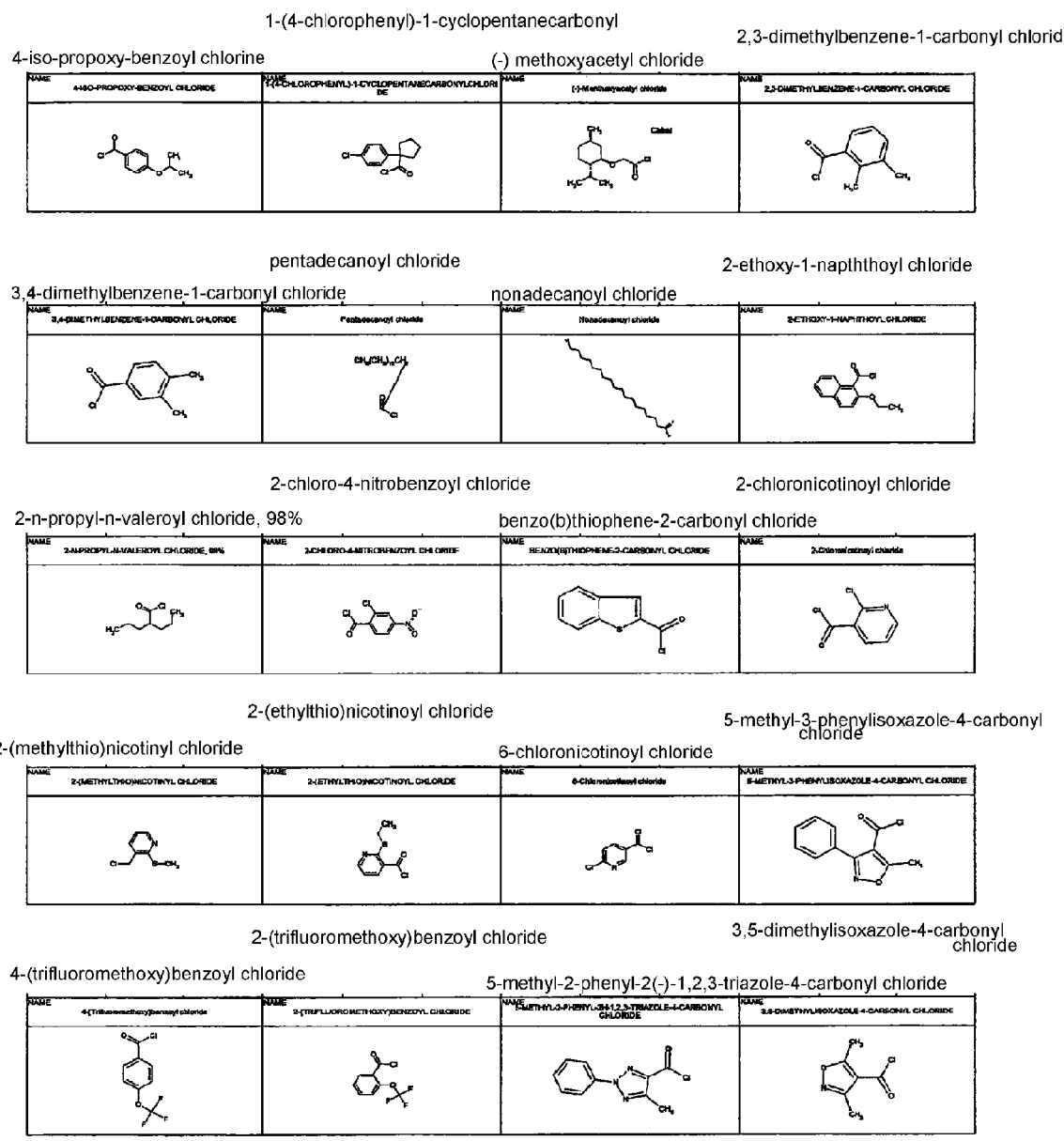
Figure 6K:
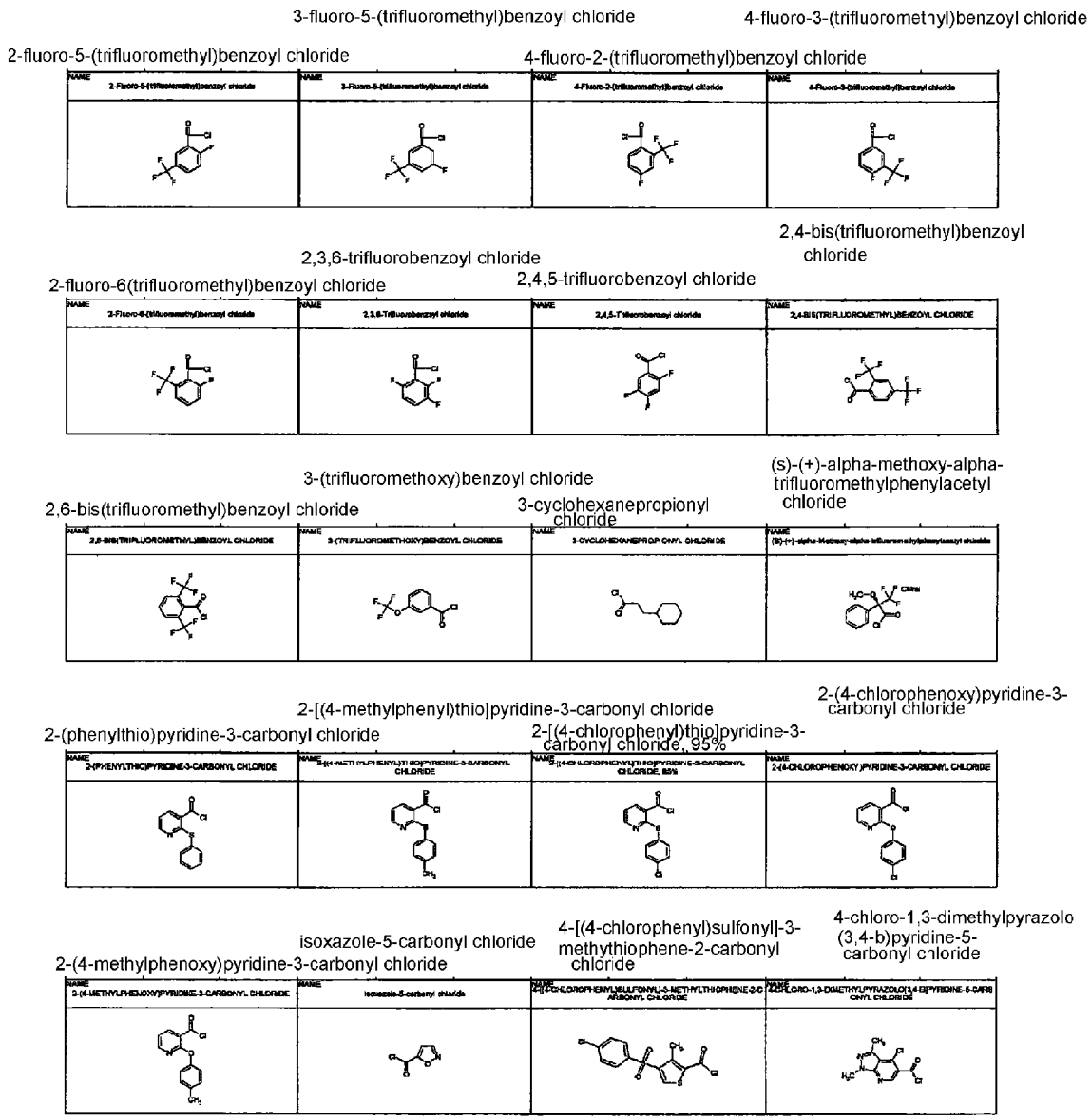
Figure 6L:
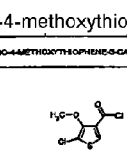
Figure 6O:
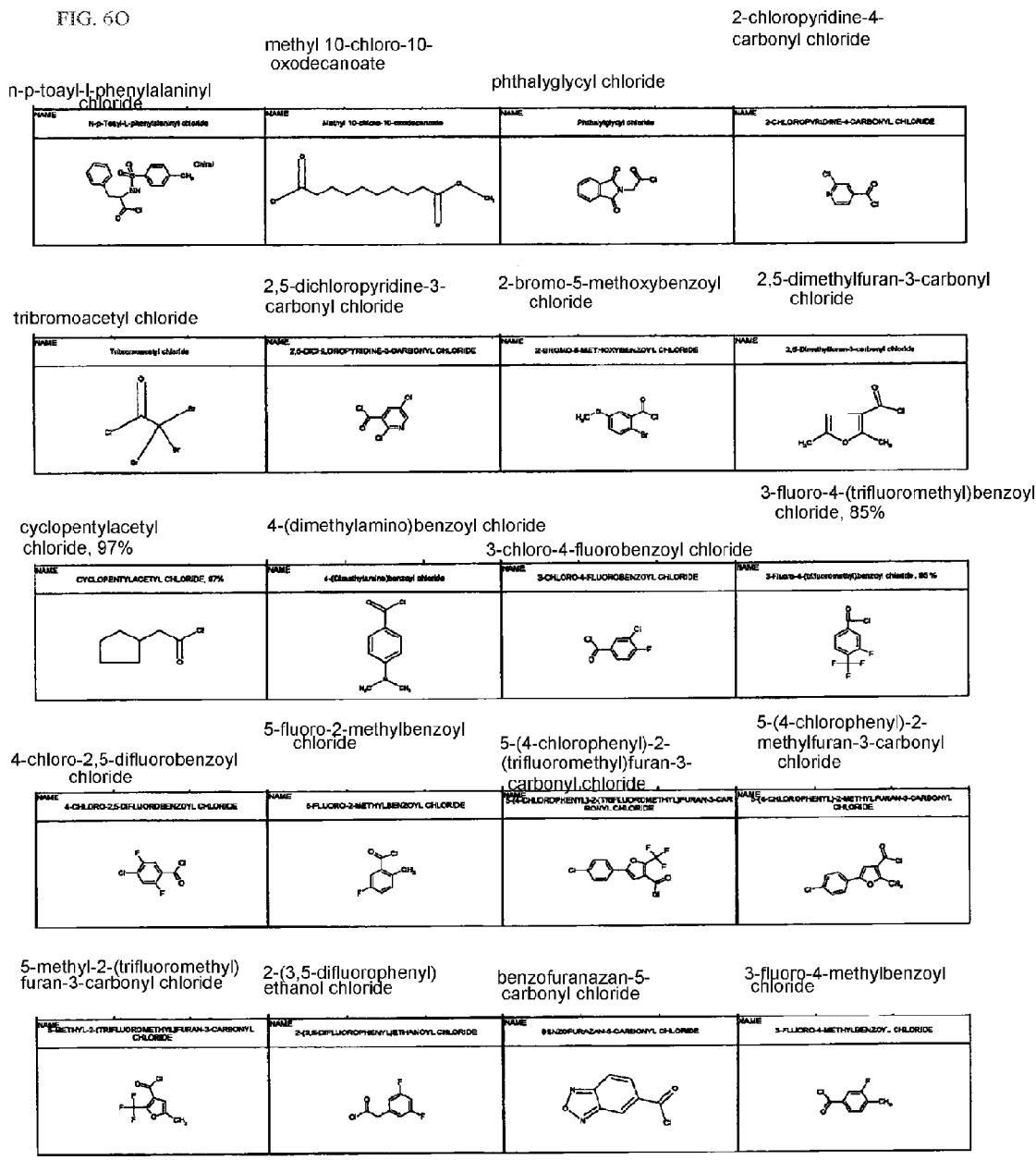
Figure 6S:
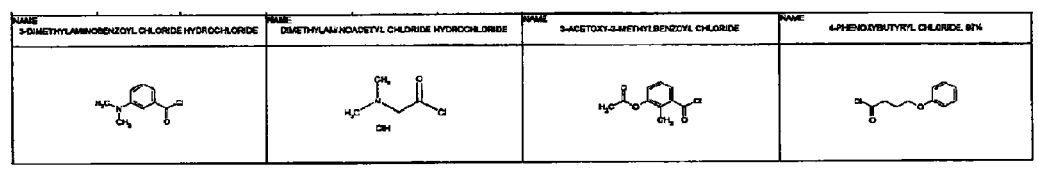
Figure 6S:
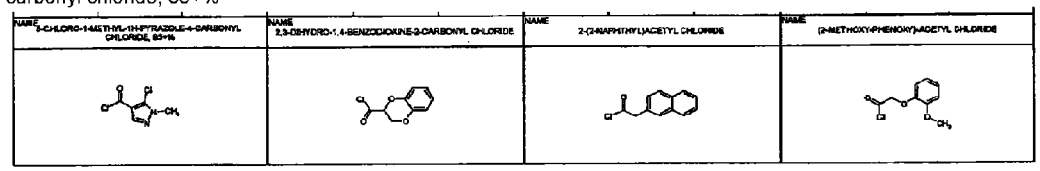
Figure 6S:
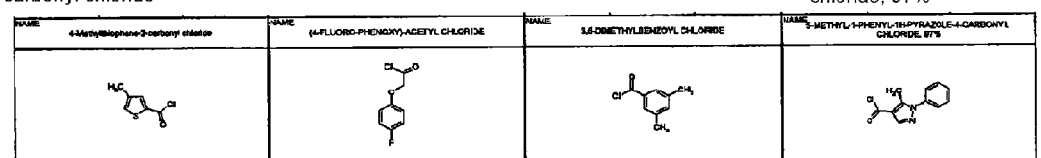
Figure 6S:
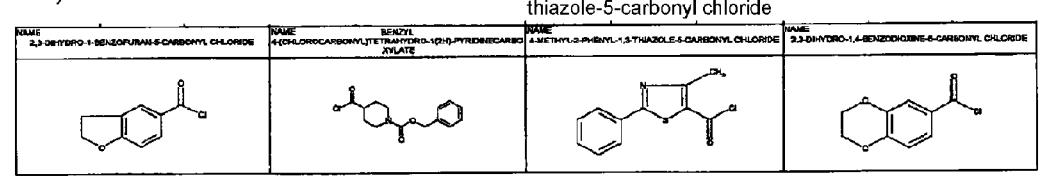
Figure 6S:
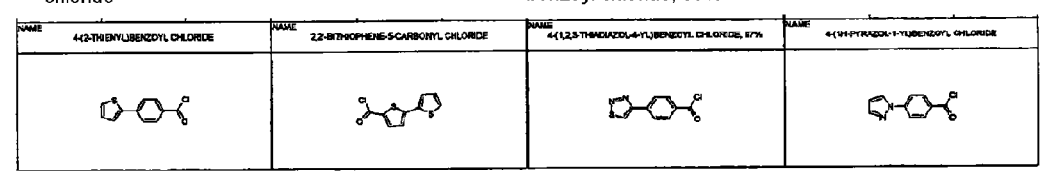

Representative compounds additionally can exhibit an in vitro selectivity index significantly greater than nifurtimox (selectivity index of 10.86), making them significantly more selective in inhibiting the growth and proliferation of *Trypanosoma cruzi*. Comparison of the antityponosomal activities with cytotoxicity on Balb/C 3T3 mouse fibroblast cell line shows certain of these compounds show far better selectivity than nifurtimox as seen from the selectivity indices values (Table 1 and FIG. 5), such as seen for a cyclic imido-substituted 1,4-naphthoquinone, a phthalimidyl-substituted 1,4-napthoquinone, an open-chain imido-substituted 1,4-naptho-quinione and a meta-halogenated aryl imido-substituted 1,4-naphthoquinone. For instance, the selectivity indices for IMDNQ1, IMDNQ2, IMDNQ3 and IMDNQ10 were 60.25, 53.97, 31.83 and 275.3, respectively. While the dibutyrylamino derivative (IMDNQ3) is the most potent with an IC$_{50}$ value of 0.7 μM against *Trypanosoma cruzi*, and is more cytotoxic to the mouse fibroblast cells (IC$_{50}$=21.67 μM), its potent activity in vitro gives it a good selectivity index of 31.83, which is approximately 300% better than Nifurtimox. A cyclic imido-substituted 1,4-naphthoquinone can show potent antitrypanosomal activity while being relatively non-toxic, as seen from IMDNQ1 (potency IC$_{50}$=2.77 μM for IMDNQ1 and non-toxicity to mouse fibroblast cell, IC$_{50}$ value of 165.9 μM for IMDNQ1). A phthalimidyl-substituted 1,4-naphthoquinone can show potent antitrypanosomal activity while being relatively non-toxic, as seen from IMDNQ2 (potency IC$_{50}$=4.89 μM for IMDNQ2 and non-toxicity to mouse fibroblast cell, IC$_{50}$ value of 253.7 μM for IMDNQ2).

A diaryl imido analog in which each aryl ring has meta-halo substitution in the diarylimido moiety may be preferred. IMDNQ10 is a diaryl imido analog with a meta-chloro-substituent on each of the aryl groups and thus significantly differs structurally from the cyclic imido-substituted derivative IMDNQ1, the phthalimidyl-substituted derivative IMDNQ2 and the open chain imido-substituted 1,4-naphthoquinone derivative IMDNQ3. IMDNQ10 exhibited an unexpected combination of useful properties. The IMDNQ10 analog exhibited potent antitrypanosomal activity with an IC$_{50}$ value of 2.23 μM against *Trypanosoma cruzi*, was non-cytotoxic to the mouse fibroblast cell (IC$_{50}$ value of 610.9 μM), and yielded a calculated selectivity index of 275.3, which was unexpectedly about 25 times better than nitfurtimox.

TABLE 1

| | Antitrypanocidal activity IC$_{50}$ (μM) | Cytotoxicity IC$_{50}$ (μM) | Selectivity Index (Cytotoxicity/Activity) |
| --- | --- | --- | --- |
| Nifurtimox | 10.67 ± 1.01 | 114.0 ± 1.03 | 10.86 ± 093 |
| IMDNQ1 | 2.77 ± 0.15 | 165.9 ± 1.24 | 60.25 ± 2.79 |
| IMDNQ2 | 4.83 ± 0.60 | 253.7 ± 1.87 | 53.97 ± 5.95 |
| IMDNQ3 | 0.70 ± 0.10 | 21.67 ± 1.45 | 31.83 ± 3.17 |
| IMDNQ4 | 4.93 ± 0.64 | 35.50 ± 1.76 | 7.43 ± 0.97 |
| IMDNQ5 | 2.27 ± 0.15 | 12.83 ± 0.73 | 5.70 ± 0.06 |
| IMDNQ6 | 1.51 ± 0.01 | 14.17 ± 1.42 | 9.43 ± 0.94 |

TABLE 1-continued

|  | Antitrypanocidal activity IC$_{50}$ (μM) | Cytotoxicity IC$_{50}$ (μM) | Selectivity Index (Cytotoxicity/Activity) |
|---|---|---|---|
| IMDNQ7 | 1.27 ± 0.15 | 17.83 ± 2.21 | 14.23 ± 1.62 |
| IMDNQ8 | 2.67 ± 0.33 | 26.50 ± 1.61 | 10.17 ± 0.97 |
| IMDNQ9 | 4.07 ± 0.23 | 21.83 ± 1.88 | 5.43 ± 0.69 |
| IMDNQ10 | 2.23 ± 0.15 | 610.9 ± 10.27 | 275.3 ± 13.73 |
| IMDNQ11 | 6.10 ± 0.38 | 19.67 ± 3.71 | 3.20 ± 0.44 |

Tublin Assembly Assay

In principle, a mode of action (mechanism of action against *Trypanosoma cruzi*) of the imido-substituted 1,4-naphthoquinone compounds is by tublin polymerization inhibition. It may not be the exclusive mode of action. A higher tubulin polymerization inhibition IC$_{50}$ value compared to antitrypanosomal activity IC50 value against *Trypanosoma cruzi* suggests other mechanisms in addition to tubulin inhibition may be responsible for the differences.

Tubulin assembly assays were conducted to assess tubulin polymerization inhibition. The assays were conducted in a 96-well microplate. Assembly reactions were conducted in a buffer containing 0.1 M PIPES (pH 6.9), 1 mM EGTA, 5 mM Mgcl, 1.2 mg/ml purified *Trypanosoma cruzi* tublin, at concentrations (0.6-40 μM) of the imido-substituted 1,4-naphthoquinone (IMDNQ 1-IMDNQ 11). Components of the reaction mixtures were added to the microplate and assembly was initiated by the addition of 1 mM GTP. The assembly reactions were assayed photometrically by measuring the absorbance at 405 nm using a microplate reader at 30° C.

The results of the tubulin assembly assay for IMDNQ 1, 2, 3, 10 and 11 are presented in Table 2.

TABLE 2

|  | Tubulin polymerization Inhibition IC$_{50}$(μM) |
|---|---|
| Nifurtimox |  |
| IMDNQ1 | 6 |
| IMDNQ2 | 12 |
| IMDNQ3 | 3.2 |
| IMDNQ10 | 8 |
| IMDNQ11 | >40 |

The eleven representative imido-substituted 1,4-naptho-quinones IMDNQ1 through IMDNQ11 can inhibit tubulin polymerization.

In general, a lower value for Tubulin polymerization Inhibition IC$_{50}$(μM) is indicative of greater inhibition of tublin polymerization. The data appear consistent with the antitrypanocidal activity against *Trypanosoma cruzi* reported in Table 1.

REFERENCES

The complete disclosure of each of the following references is incorporated herein by reference:
1. Akinboye et al., Acta Cryst. E65, o24 (2009)
2. Akinboye et al., Acta Cryst. E65, o277 (2009)
3. Andrade et al., Short Report: Benzidazole Efficacy Among *Trypanosoma Cruzi*-infected Adolescents After a Six-year Follow-up, Am. J. Trop. Med. Hyg., 71(5):594-597 (2004)
4. Bakare, O., et al, Synthesis and MEK1 inhibitory activities of imido-substituted 2-chloro-1,4-naphthoquinones. Bioorg. Med. Chem., 11, 3165-3170 (2003) (2003);
5. Berhe, S., et al., Microwave-assisted synthesis of imido-substituted 2-chloro-1,4-naphthoquinone derivatives and their cytotoxic activities on three human prostate cancer cell lines, Lett. Drug Des. Discov., 5, 485-488 (2008)
6. Copeland, R. L., Jr., Das, J. R., Bakare, O., Enwerem, N. M., Berhe, S., Hillaire, K., White, D., Beyene, D., Kassim, O. O., and Kanaan, Y. M., Cytotoxicity of 2,3-dichloro-5, 8-dimethoxy-1,4-naphthoquinone in androgen-dependent and -independent prostate cancer cell lines. *Anticancer Res.*, 27, 1537-1546 (2007)
7. Coura, R., and De Castro, S. L., A critical review on Chagas' disease chemotherapy. *Mem. do Inst. Oswaldo Cruz*, 97, 3-24 (2002)
8. Ferreira, R. C., and Ferreira, L. C., Mutagenicity of nifurtimox and benznidazole in the *Salmonella*/microsome assay. *Braz. J. Med. Biol. Res.*, 19, 19-25 (1986)
9. Galvão et al., PCR Assay for Monitoring *Trypanosoma cruzi* Parasitemia in Childhood after Specific Chemotherapy, J. Clin. Microbiology, 5066-70 (November 2003)
10. Gomes et al., Chagas disease diagnosis: comparative analysis of parasitologic, molecular and serological methods, Am. J. Trp. Med. Hyg. 60:205-210 (1999)
11. Hotez, P. J., Neglected infections of poverty in the United States of America. *PLoS Negl. Trop. Dis.*, 2, e256 (2008)
12. Huang, L. J., Chang, F. C., Lee, K. H., Wang, J. P., Teng, C. M., and Kuo, S. C., Synthesis and antiplatelet, antiinflammatory, and antiallergic activities of substituted 3-chloro-5,8-dimethoxy-1,4-naphthoquinone and related compounds. *Bioorg. Med. Chem.*, 6, 2261-2269 (1998)
13. Kartoflitskaya, A. P., Stepanyuk, G. I., Yushkova, V. V., Marintsova, N. G., and Novikov, V. P. Synthesis and the anti hypoxic and antiischemic activity of some 2-chloro-1, 4-naphthoquinone derivatives. *Pharm. Chem. J.*, 31, 291-292 (1997)
14. Melo, M. E., and Ferreira, L. C., Screening the mutagenic activities of commonly used antiparasite drugs by the Simultest, a simplified *Salmonella*/microsome plate incorporation assay. *Rev. Inst. Med. Trop. Sao Paulo*, 32, 269-274 (1990)
15. Nagel, R., and Nepomnaschy, I., Mutagenicity of 2 antichagasic drugs and their metabolic deactivation. *Mutat. Res.*, 117, 237-242 (1983)
16. Perez et al., Synthesis of Iodinated Naphthoquinones Using Morpholine-Iodine Complex, Synthetic Communications, 34(18):3389-3397 (2004)
17. Ramos, E. I., Garza, K. M., Krauth-Siegel, R. L., Bader, J., Martinez, L. E., and Maldonado, R. A., 2,3-diphenyl-1,4-naphthoquinone: a potential chemotherapeutic agent against *Trypanosoma cruzi*. *J. Parasitol.*, 95, 461-466 (2009)
18. Salas, C., Tapia, R. A., Ciudad, K., Armstrong, V., Oreliana, M., Kemmerling, U., Ferreira, J., Maya, J. D., and Morello, A., *Trypanosoma cruzi*: activities of lapachol and alpha- and beta-lapachone derivatives against epimastigote and trypomastigote forms. *Bioorg. Med. Chem.*, 16, 668-674 (2008).
19. Schofield, C. J., and Kabayo, J. P., Trypanosomiasis vector control in Africa and Latin America. *Parasites Vectors*, 1, 24 (2008)
20. Silva, R., Costa, E., Trindade, U., Teixeira, D., Pinto, M., Santos, G., Malta, V., De Simone, C., Pinto, A., and De Castro, S., Synthesis of naphthofuranquinones with activity against *Trypanosoma cruzi*. *Eur. J. Med. Chem.*, 41, 526-530 (2006)
21. Tandon, V. K., Singh, R. V., and Yadav, D. B., Synthesis and evaluation of novel 1,4-naphthoquinone derivatives as antiviral, antifungal and anticancer agents. *Bioorg. Med. Chem. Lett.*, 14, 2901-2904 (2004).

While the invention has been described in terms of preferred embodiments, those skilled in the art will recognize that the invention can be practiced with modification within the spirit and scope of the appended claims.

The invention claimed is:

1. A method selected from the group consisting of:
   (a) a method of inhibiting proliferation of *Trypanosoma cruzi* in a patient in need of treatment comprises administering to said patient an antitrypanosomal effective amount of an imido-substituted 1,4-naphthoquinone represented by the general formula:

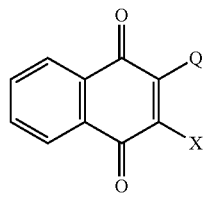

wherein X is alkoxy (cyclic or alicyclic) or aryloxy, and Q represents the imido-substitutent bonded to the 1,4-naphthoquinone moiety through the imido nitrogen,
   (b) a method of inhibiting tubulin polymerization in *Trypanosoma cruzi* in a patient in need of treatment comprises administering to said patient, in an amount effective for inhibiting tubulin polyermization, an imido-substituted 1,4-naphthoquinone represented by the general formula:

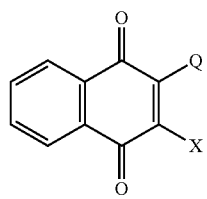

wherein X is alkoxy (cyclic or alicyclic) or aryloxy, and Q represents the imido-substitutent bonded to the 1,4-naphthoquinone moiety through the imido nitrogen,
   (c) a method of treating Chagas disease in a patient in need of treatment comprises administering to said patient a therapeutically effective amount of an imido-substituted 1,4-naphthoquinone represented by the general formula:

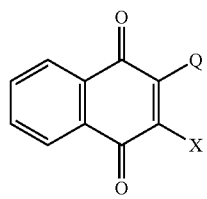

wherein X is alkoxy (cyclic or alicyclic) or aryloxy, and Q represents the imido-substitutent bonded to the 1,4-naphthoquinone moiety through the imido nitrogen, and
   (d) a method of inhibiting proliferation of *Trypanosoma cruzi* in a patient in need of treatment comprises administering to said patient an antitrypanosomal effective amount of an imido-substituted 1,4-naphthoquinone represented by the formula:

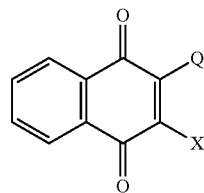

wherein X is alkoxy (cyclic or alicyclic) or aryloxy, and Q represents the imido-substitutent bonded to the 1,4-naphthoquinone moiety through the imido nitrogen, wherein Q is represented by the formula:

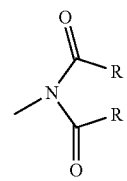

wherein in Q each R is, independently, a substituted or unsubstituted hydrocarbon, provided that one R can, optionally, be hydrogen, and provided that, optionally, R can include at least one hetero atom.

2. The method according to claim 1, wherein the imido-substituted 1,4-naphthoquinone has in vitro toxicity against *Trypanosoma cruzi* greater than nitfurtimox.

3. The method according to claim 1, wherein the imido-substituted 1,4-naphthoquinone has an in vitro selectivity index greater than nitfurtimox.

4. The method according to claim 1, wherein the imido-substituted 1,4-naphthoquinone has an $IC_{50}$ cytoxicity value against greater than 100 µM.

5. The method according to claim 1, wherein in (a), (b) or (c) Q is represented by the formula

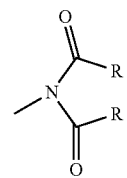

wherein each R is cyclic or acyclic, or the R groups are bonded together.

6. The method according to claim 1, wherein each R is aryl, halo-substituted aryl, aliphatic, halo-substituted aliphatic, or alkenyl.

7. The method according to claim 1, wherein X is alkoxy.

8. The method according to claim 1, wherein X is aryloxy.

9. The method according to claim 1, wherein Q is an aryl-imido substituent.

10. The method according to claim 7, wherein each R is aryl, optionally having halogen substitution.

11. The method according to claim 1, wherein the imido-substituted 1,4-naphthoquinone is represented by the formula:

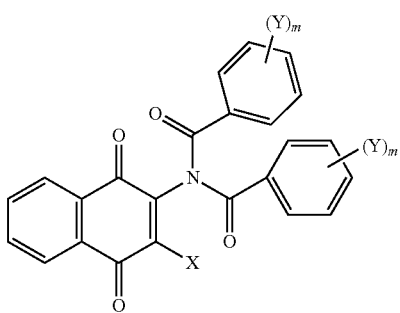

wherein X is alkoxy (cyclic alicyclic) or aryloxy, each Y, independently, represents halogen, alkoxy (cyclic or alicyclic), trifluoro methyl or alkyl, and each m, independent of the other, is 0, 1, 2, 3, 4 or 5.

12. The method according to claim 11, wherein Y is bromo, chloro or fluoro.

13. The method according to claim 1, wherein the method is (a).

14. The method according to claim 1, wherein the method is (b).

15. The method according to claim 1, wherein the method is (c).

16. The method according to claim 1, wherein the method is (d).

17. A composition for use in inhibiting proliferation of *Trypanosoma cruzi* in a mammalian patient comprising an imido-substituted 1,4-naphthoquinone represented by the general formula:

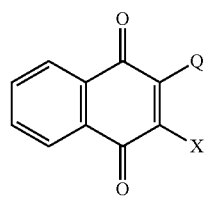

wherein X is alkoxy (cyclic or alicyclic) aryloxy, or benzyloxy; and Q represents an imido-substitutent bonded to the 1,4-naphthoquinone moiety through the imido nitrogen.

18. The composition comprising imido-substituted 1,4-naphthoquinone according to claim 17, wherein Q is represented by the formula

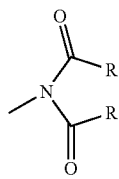

wherein in Q each R is, independently, a substituted or unsubstituted hydrocarbon, provided that one R can, optionally, be hydrogen, and provided that, optionally, R can include at least one hetero atom.

19. The composition comprising imido-substituted 1,4-naphthoquinone according to claim 18, wherein in Q at least one R is cyclic, acyclic or each R is bonded together.

20. The composition comprising imido-substituted 1,4-naphthoquinone according to claim 17, wherein said imido-substituted 1,4-naphthoquinone is represented by the formula:

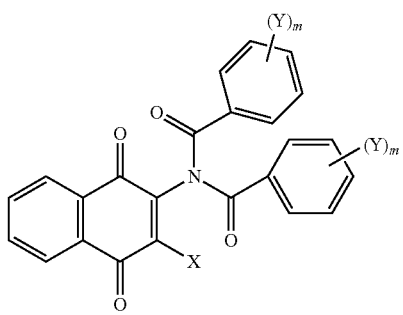

wherein X is alkoxy (cyclic or alicyclic) or aryloxy, each Y, independently, represents halogen, alkoxy (cyclic alicyclic), trifluoro methyl, trifluoromethoxy, or alkyl, and each m, independent of the other, is 0 1, 2, 3, 4 or 5.

21. The composition comprising imido-substituted 1,4-naphthoquinone according to claim 20, wherein at least one Y is bromo, chloro or fluoro.

22. A method selected from the group consisting of:
(a) a method of inhibiting proliferation of *Trypanosoma cruzi* in a patient in need of treatment comprises administering to said patient an antitrypanosomal effective amount of an imido-substituted 1,4-naphthoquinone represented by the general formula:

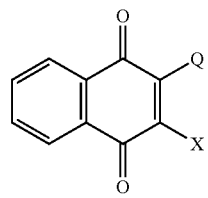

wherein X is H, trifluoro methyl, or benzyloxy; and Q represents the imido-substitutent bonded to the 1,4-naphthoquinone moiety through the imido nitrogen,
(b) a method of inhibiting tubulin polymerization in *Trypanosoma cruzi* in a patient in need of treatment comprises administering to said patient, in an amount effective for inhibiting tubulin polyermization, an imido-substituted 1,4-naphthoquinone represented by the general formula:

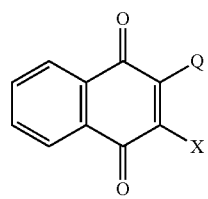

wherein X is H, alkyl, trifluoro methyl, or benzyloxy; and Q represents the imido-substitutent bonded to the 1,4-naphthoquinone moiety through the imido nitrogen, and
(c) a method of treating Chagas disease in a patient in need of treatment comprises administering to said patient a therapeutically effective amount of an imido-substituted 1,4-naphthoquinone represented by the general formula:

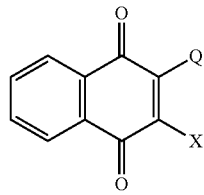

wherein X is H, alkyl, trifluoro methyl, or benzyloxy; and Q represents the imido-substitutent bonded to the 1,4-naphthoquinone moiety through the imido nitrogen, wherein the imido substituent Q is represented by the formula:

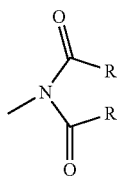

wherein in Q each R is, independently, a substituted or unsubstituted hydrocarbon, provided that one R can, optionally, be hydrogen, and provided that, optionally, R can include at least one hetero atom, and, optionally, the R groups can be bonded together.

23. A method according to claim 22, wherein said imido-substituted 1,4-naphthoquinone is represented by the formula:

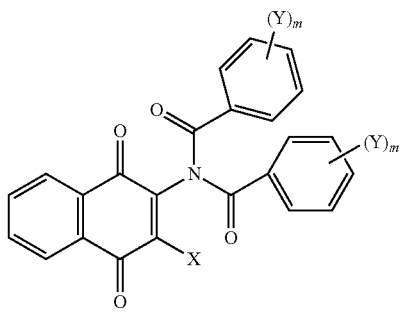

wherein X is H, alkyl, trifluoro methyl or benzyloxy, each Y, independently, represents halogen, alkoxy (cyclic alicyclic), trifluoro methyl, trifluoromethoxy, or alkyl, and each m, independent of the other, is 0, 1, 2, 3, 4 or 5.

24. The method according to claim 22, wherein the method is (a).

25. The method according to claim 22, wherein the method is (b).

26. The method according to claim 22, wherein the method is (c).

* * * * *